US007371571B2

(12) United States Patent
Barletta et al.

(10) Patent No.: US 7,371,571 B2
(45) Date of Patent: May 13, 2008

(54) RECOMBINANT MYCOBACTERIA OVEREXPRESSING D-ALANINE LIGASE GENE AND USES THEREFORE

(75) Inventors: Raul G. Barletta, Lincoln, NE (US); Zhengyu Feng, Austin, TX (US)

(73) Assignee: Board of Regents University of Nebraska - Lincoln, Lincoln, NE (US)

( * ) Notice: Subject to any disclaimer, the term of this patent is extended or adjusted under 35 U.S.C. 154(b) by 386 days.

(21) Appl. No.: 10/738,938

(22) Filed: Dec. 17, 2003

(65) Prior Publication Data

US 2004/0241830 A1 Dec. 2, 2004

Related U.S. Application Data

(60) Provisional application No. 60/434,200, filed on Dec. 17, 2002.

(51) Int. Cl.
*C12N 15/00* (2006.01)
*C12N 1/21* (2006.01)
*C12Q 1/00* (2006.01)
*C12P 21/06* (2006.01)
*C12N 9/00* (2006.01)
*C07K 14/00* (2006.01)
*C07H 21/04* (2006.01)

(52) U.S. Cl. ............... 435/320.1; 435/252.3; 435/253.1; 435/69.1; 435/183; 435/4; 530/350; 536/23.2

(58) Field of Classification Search ............. 435/253.1, 435/320.1, 69.1, 183, 252.3, 4; 530/350; 536/23.2
See application file for complete search history.

(56) References Cited

U.S. PATENT DOCUMENTS

2003/0133952 A1 7/2003 Barletta et al.

OTHER PUBLICATIONS

Brown, Barbara A., et al., "*Mycobacterium wolinskyi* Sp. Nov. and *Mycobacterium goodii* Sp. Nov., Two New Rapidly Growing Species Related to *Mycobacterium smegmatis* and Associated with Human Would Infections: A Cooperative Study from the International Working Group on Mycobacterial Taxonomy", *International Journal of Systematic Bacteriology.* 1999, vol. 49, p. 1493-1511.
Hingley-Wilson, Suzanne M., et al., "Survival Perspectives from the World's Most Successful Pathogen, *Mycobacterium tuberculosis*", *Nature Immunology.* Oct. 2003, vol. 4, No. 10, p. 949-955.
Lagier, Beatrice, et al., "Identification of Genetic Loci Implicated in the Survival of *Mycobacterium smegmatis* in Human Mononuclear Phagocytes", *Molecular Microbiology.* 1998, vol. 29, No. 2, p. 465-475.
Piddington, Debra L., et al., "Cu,Zn Superoxide Dismutase of *Mycobacterium tuberculosis* Contributes to Survival in Activated Macrophages That Are Generating an Oxidative Burst", *Infection and Immunity.* Aug. 2001, vol. 69, No. 8, p. 4980-4987.

Harth, Gunter, et al., "High-Level Heterologous Expression and Secretion in Rapidly Growing Nonpathogenic *Mycobacteria* of Four Major *Mycobacterium tuberculosis* Extracellular Proteins Considered To Be Leading Vaccine Candidates and Drug Targets", *Infection and Immunity*, Jun. 1997, vol. 65, No. 6, p. 2321-2328.
MacGowan, Alasdair, et al., "In Vitro Models, In Vivo Models, and Pharmacokinetics: What Can We Learn from In Vitro Models?", *CID.* 2001 vol. 33 (Suppl 3), p. S214-S220.
Orme, Ian M. and Collins, Frank M., "Mouse Model of Tuberculosis". Chapter 8, p. 113-134. *Tuberculosis: Pathogenesis, Protection and Control*, Barry R. Bloom (ed.), 1994, American Society for Microbiology, Washington, DC 20005.
McMurray, David N., "Guinea Pig Model of Tuberculosis". Chapter 9, p. 135-147. *Tuberculosis: Pathogenesis, Protection and Control*, Barry R. Bloom (ed.), 1994, American Society for Microbiology, Washington, DC 20005.
Dannenberg, Jr., Arthur M., "Rabbit Model of Tuberculosis", Chapter 10, p. 149-156. *Tuberculosis: Pathogenesis, Protection and Control*, Barry R. Bloom (ed.), 1994, American Society for Microbiology, Washington, DC 20005.
Thoen, Charles O. "Tuberculosis in Wild and Domestic Mammals". Chapter 11, p. 157-162. *Tuberculosis: Pathogenesis, Protection and Control*, Barry R. Bloom (ed.), 1994, American Society for Microbiology, Washington, DC 20005.
Jacobs, Jr., William R. "*Mycobacterium tuberculosis:* A Once Genetically Intractable Organism", p. 1-16, *Molecular Genetics of Mycobacteria*, G.F. Hatful and W.R. Jacobs, Jr., (eds.), 2000, ASM Press, Washington, D.C.
Barletta, Raul G., et al. "Vaccines Against Intracellular Pathogens", *Subcellular Biochemistry.* 2000, vol. 33, p. 559-599.
Feng, Zhengyu, and Barletta, Raúl, "Roles of *Mycobacterium smegmatis* D-Alanine:D-Alanine Ligase and D-Alanine Racemase in the Mechanisms of Action of and Resistance to the Peptidoglycan Inhibitor D-Cycloserine", *Antimicrobial Agents and Chemotherapy.* 2003, vol. 47, No. 1, p. 283-291.
Chacon, Ofelia, et al., "*Mycobacterium smegmatis* D-Alanine Racemase Mutants Are Not Dependent on D-Alanine for Growth", *Antimicrobial Agents and Chemotherapy.* 2002, vol. 46, No. 1, p. 47-54.
Cáceres, Nancy E., et al., "Overexpression of the D-Alanine Racemase Gene Confers Resistance to D-Cycloserine in *Mycobacterium smegmatis*", *Journal of Bacteriology.* Aug. 1997, vol. 179, No. 16, p. 5046-5055.
Zhengyu, Feng, et al., "*Mycobacterium smegmatis* L-Alanine Dehydrogenase (Ald) Is Required for Proficient Utilization of Alanine as a Sole Nitrogen Source and Sustained Anaerobic Growth", *Journal of Bacteriology.* Sep. 2002, vol. 184, No. 18, p. 5001-5010.
Kamogashira, Takashi and Takegata, Setsuko, "A Screening Method for Cell Wall Inhibitors Using a D-Cycloserine Hypersensitive Mutant", *The Journal of Antibiotics.* Jun. 1988, vol. XLI, No. 6, p. 803-806.

(Continued)

*Primary Examiner*—Delia M. Ramirez
(74) *Attorney, Agent, or Firm*—Stinson Morrison Hecker LLP

(57) ABSTRACT

Recombinant mycobacterial strains which overproduce essential biosynthetic enzymes of pathogenic mycobateria are provided. These strains overproduce enzymes involved in the synthesis and incorporation of D-alanine into mycobacterial peptidoglycan, the backbone of the mycobacterial cell wall. These overproducing strains may be used as reference strains in in vitro screening methods to identify antimycobacterial agents.

10 Claims, 7 Drawing Sheets

OTHER PUBLICATIONS

Strych, Ulrich, et al., "Characterization of the Alanine Racemases from Two *Mycobacteria*", *FEMS Microbiology Letters.* 2001, vol. 196, p. 93-98.

Copié, Valérie, et al., "Inhibition of Alanine Racemase by Alanine Phosphonate: Detection of an Imine Linkage to Pyridoxal 5'—Phosphate in the Enzyme-Inhibitor Complex by Solid-State $^{15}$N Nuclear Magnetic Resonance". *Biochemistry,* 1988, vol. 27, p. 4966-4970.

Heaton, Michael P., et al., "Controlled Lysis of Bacterial Cells Utilizing Mutants with Defective Synthesis of D-Alanine", *Can. J. Microbiol.,* 1988, vol. 34, p. 256-261.

Patchett, Arthur A., et al., "Antibacterial Activities of Fluorovinyl- and Chlorovinylglycine and Several Derived Dipeptides", *Antimicrobial Agents and Chemotherapy.* Mar. 1988, vol. 32, No. 3, p. 319-323.

Lambert, Mary P., and Neuhaus, Francis C., "Mechanism of D-Cycloserine Action: Alanine Racemase from *Escherichia coli* W", *Journal of Bacteriology.* 1972, vol. 110, No. 3, p. 978-987.

Hols, Paxcal, et al, "Conversion of *Lactococcus Lactis* from Homolactic to Homoalanine Fermentation through Metabolic Engineering", *Nature Biotechnology.* Jun. 1999, vol. 17, p. 588-592.

Tauch, Andreas, et al., "The Alanine Racemase Gene *alr* is an Alternative to Antibiotic Resistance Genes in Cloning Systems for Industrial *Corynebacterium Glutamicum* Strains", *Journal of Biotechnology.* 2002, vol. 99, p. 79-91.

Arias, Cesar A., et al, "Serine and Alanine Racemase Activities of VanT: a Protein Necessary for Vancomycin Resistance in *Enterococcus Gallinarum* BM4174", *Microbiology.* 2000, vol. 146, p. 1727-1734.

Thompson, Robert J., et al, "Pathogenicity and Immunogenicity of a *Listeria monocytogenes* Strain That Requires D-Alanine for Growth", *Infection and Immunity.* Aug. 1998, vol. 66, No. 8, p. 3552-3561.

Hols, P., et al., "The Alanine Racemase Gene is Essential for Growth of *Lactobacillus plantarum*", *Journal of Bacteriology.* Jun. 1997, vol. 179, No. 11, p. 3804-3807.

Neidhart, David J., et al., "X-ray Crystallographic Studies of the Alanine-specific Racemase from *Bacillus stearothermophilus*", *The Journal of Biological Chemistry.* 1987, vol. 262, No. 32, p. 15323-15326.

Braunstein, Miriam, et al., "Genetic Methods for Deciphering Virulence Determinants of *Mycobacterium tuberculosis*", *Virulence and Essential Gene Identification.* 2002 p. 67-99.

Tyagi, Jaya S. and Sharma, Deepak, "*Mycobacterium smegmatis* and Tuberculosis", *Trends in Microbiology.* Feb. 2002, vol. 10, No. 2, p. 68-69.

David, Hugo L., et al., "Susceptibility of Mycobacterial D-Alanyl-D-Alanine Synthetase to D-Cycloserine", *American Review of Respiratory Disease.* 1969, vol. 100, p. 579-581.

Neuhaus, Francis C. "The Enzymatic Synthesis of D-Alanyl-D-alanine. I. Purification and Properties of D-Alanyl-D-Alanine Synthetase", *Journal of Biological Chemistry.* Mar. 1962, vol. 237, No. 3, p. 778-786.

Peteroy, Marcy, et al., "Characterization of a *Mycobacterium smegmatic* Mutant That Is Simultaneously Resistant to D-Cycloserine and Vancomycin", *Antimicrobial Agents and Chemotherapy.* Jun. 2000, vol. 44, No. 6, p. 1701-1704.

Manning, James M., et al., "Inhibition of Bacterial Growth by β-Chloro-D-Alanine", *Proc. Nat. Acad. Sci.* Feb. 1974, vol. 71, No. 2, p. 417-421.

David, Suzana, "Synergic Activity of D-Cycloserine and β-Chloro-D-Alanine Against *Mycobacterium tuberculosis*", *Journal of Antimicrobial Chemotherapy.* 2001, vol. 47, p. 203-206.

Marshall, C. Gary and Wright, Gerald D., "Dd1N from Vancomycin-Producing *Amycolatopsis orientalis* C329.2 Is a VanA Homologue with D-Alanyl-D-Lactate Ligase Activity", *Journal of Bacteriology.* Nov. 1998, vol. 180, No. 21, p. 5792-5795.

Rastogi, Nalin, et al., "Enhancement of Drug Susceptibility of *Mycobacterium avium* by Inhibitors of Cell Envelope Synthesis", *Antimicrobial Agents and Chemotherapy.* May 1990, vol. 34, No. 5, p. 759-764.

Dutka-Malen, Sylvie, et al., "Sequence of the vanC Gene of *Enterococcus gallinarum* BM4174 encoding a D-Alanine:D-Alanine Ligase-Related Protein Necessary for Vancomycin Resistance", *Gene.* 1992, vol. 112, p. 53-58.

Belanger, Aimee E. and Inamine, Julia M., "Genetics of Cell Wall Biosynthesis", *Molecular Genetics of Mycobacteria.* Hatfull, G.F. and Jacobs, W.R. (Eds.), ASM Press, Washington, D.C., 2000, p. 191-202.

Reitz, Richard H., et al., "The Biochemical Mechanisms of Resistance by *Streptococci* to the Antibiotics D-Cycloserine and O-Carbamyl-D-Serine", *Biochemistry.* Aug. 1967, vol. 6, No. 8, p. 2561-2570.

Walsh, Christoper T., "Enzymes in the D-Alanine Branch of Bacterial Cell Wall Peptidoglycan Assembly", *Journal of Biological Chemistry.* 1989, vol. 264, No. 5, p. 2393-2396.

David, Hugo L., "Resistance to D-Cycloserine in the Tubercle Bacilli: Mutation Rate and Transport of Alanine in Parental Cells and Drug-Resistant Mutants", *Applied Microbiology.* May 1971, vol. 21, No. 5, p. 888-892.

Zygmunt, Walter A., "Antagonism of D-Cycloserine Inhibition of Mycobacterial Growth By D-Alanine", *J. Bacteriol.* 1963, vol. 85, p. 1217-1220.

Yew, Wing Wai, et al., "Adverse Neurological Reactions in Patients with Multidrug-Resistant Pulmonary Tuberculosis After Coadministration of Cycloserine and Ofloxacin", *Clinical Infectious Diseases.* Aug. 1993, vol. 17, 288-289.

Kaufman, Darrell and Manley, William F., "A New Procedure for Determining DL Amino Acid Ratios in Fossels Using Reverse Phase Liquid Chromatography", 1998. *Quaternary Geochronology,* vol. 17, p. 987-1000.

Neuhaus, Francis C., "D-Cycloserine and O-Carbamyl-D-serine", *Antibiotics—vol. 1, Mechanism of Action.* Gottlieb, D and Shaw, Paul D. (eds.), Springer-Verlag New YorK Inc., 1967, p. 40-83.

```
                      SEQUENCE LISTING

<160> NUMBER OF SEQ ID NOS: 8

<210> SEQ ID NO 1
<211> LENGTH: 18
<212> TYPE: DNA
<213> ORGANISM: Artificial
<220> FEATURE:
<223> OTHER INFORMATION: SMDDLCF PRIMER

<400> SEQUENCE: 1
cgcataaggc caggtcag                                                  18

<210> SEQ ID NO 2
<211> LENGTH: 17
<212> TYPE: DNA
<213> ORGANISM: Artificial
<220> FEATURE:
<223> OTHER INFORMATION: SMDDLCR PRIMER

<400> SEQUENCE: 2
cgaaaaaccc gtcgtgc                                                   17

<210> SEQ ID NO 3
<211> LENGTH: 19
<212> TYPE: DNA
<213> ORGANISM: Artificial
<220> FEATURE:
<223> OTHER INFORMATION: DDLATBU PRIMER

<400> SEQUENCE: 3
```

```
gctaagtgcc gatcgcaag                                                    19

<210> SEQ ID NO 4
<211> LENGTH: 19
<212> TYPE: DNA
<213> ORGANISM: Artificial
<220> FEATURE:
<223> OTHER INFORMATION: DDLATBD PRIMER

<400> SEQUENCE: 4
ataacgctgc tgctgggtc                                                    19

<210> SEQ ID NO 5
<211> LENGTH: 23
<212> TYPE: DNA
<213> ORGANISM: Artificial
<220> FEATURE:
<223> OTHER INFORMATION: TBDDLEXF PRIMER

<400> SEQUENCE: 5
cgggatccgt gagtgctaac gac                                               23

<210> SEQ ID NO 6
<211> LENGTH: 24
<212> TYPE: DNA
<213> ORGANISM: Artificial
<220> FEATURE:
<223> OTHER INFORMATION: TBDDLEXR PRIMER

<400> SEQUENCE: 6
cggaagcttg tgccgatcgc aagc                                              24

<210> SEQ ID NO 7
<211> LENGTH: 21
<212> TYPE: DNA
<213> ORGANISM: Artificial
<220> FEATURE:
<223> OTHER INFORMATION: SMDDLPE PRIMER

<400> SEQUENCE: 7
aaacgctccg gatcgaggtt g                                                 21

<210> SEQ ID NO 8
<211> LENGTH: 18
<212> TYPE: DNA
<213> ORGANISM: Artificial
<220> FEATURE:
<223> OTHER INFORMATION: TBDDLPE PRIMER

<400> SEQUENCE: 8
gagatggcgt gctcgttg                                                     18
```

RECOMBINANT MYCOBACTERIA OVEREXPRESSING D-ALANINE LIGASE GENE AND USES THEREFORE

CROSS-REFERENCE TO RELATED APPLICATIONS

This application is related to U.S. Provisional Application Ser. No. 60/434,200, filed on Dec. 17, 2002, which is incorporated herein by reference.

STATEMENT REGARDING FEDERALLY SPONSORED RESEARCH OR DEVELOPMENT

The present invention was sponsored by the United States Department of Agriculture under USDA Cooperative State Research Service Project Grant No. NEB 14-108 and the National Institute of Health under contract number RO3 A1051176-01. The government may have certain rights in the invention.

BACKGROUND OF THE INVENTION

The present invention relates to recombinant mycobacterial strains overexpressing essential biosynthetic enzymes of pathogenic mycobacteria and to methods for using these strains. More specifically, the present invention relates to recombinant mycobacteria strains overexpressing D-alanine ligase (Ddl) and the use of such strains in in vitro methods for identifying antimycobacterial agents directed against Ddl.

The bacterial cell wall is an ideal target for drug design since similar structures and biosynthetic pathways are absent from mammalian hosts. The lipid-rich mycobacterial cell wall acts as an efficient permeability barrier (Brennan and Nikaido, 1995). Peptidoglycan, the backbone of this structure, contains the D-amino acids D-alanine, D-glutamate, and diaminopimelate, which may contribute to its stability against proteolytic degradation. D-Alanine is one of the central molecules of the cross-linking step of peptidoglycan assembly. Peptidoglycan biosynthesis in mycobacteria follows pathways similar to those in other eubacteria (Belanger and Inamine, 2000). There are three enzymes involved in the D-alanine branch of peptidoglycan biosynthesis: the pyridoxal phosphate-dependent D-alanine racemase (Alr), the ATP-dependent D-alanine:D-alanine ligase (Ddl), and the ATP-dependent D-alanine:D-alanine-adding enzyme (MurF) (Walsh, 1989). D-Cycloserine (DCS; 4-amino-3-isoxazolidinone) is a rigid analog of D-alanine and targets both Alr and Ddl in *Escherichia coli* (Lambert and Neuhaus, 1992; Neuhaus, 1967). DCS also inhibits *Mycobacterium tuberculosis* Alr and Ddl enzymes (David et al., 1969; Strych et al., 2001), suggesting that both Alr and Ddl are targets of DCS in mycobacteria.

DCS is effective against mycobacteria and is recommended to treat multidrug-resistant *M. tuberculosis* in the DOTS-Plus management plan (Farmer, 2001; World Health Organization, 2000). However, undesirable side effects restrict its use in human chemotherapy (Yew et al., 1993). Nonetheless, the potent bactericidal effect of DCS against mycobacteria makes this drug an attractive prototype compound to develop novel antimycobacterial agents. In addition, identification of the lethal target(s) of DCS action would allow for the rational design of new antimycobacterial drugs, structurally related or unrelated to DCS, targeting enzymes of the D-alanine pathway of peptidoglycan biosynthesis. Moreover, these types of inhibitors may weaken the cell wall and act synergistically with other antimicrobial agents (Rastogi et al., 1990). In the early 1970s, David (1971) isolated and characterized step-wise DCS-resistant *M. tuberculosis* mutants that showed either normal or reduced cellular permeability to DCS and speculated that Alr plays only a minor role in the mechanism of action of DCS. *Mycobacterium smegmatis*, a nonpathogenic species, is a useful model to study drug resistance mechanisms in pathogenic mycobacteria, especially when conserved cellular processes are involved (Reyrat and Kahn, 2001; Tyagi and Sharma, 2002). Peteroy et al. (2000) described the isolation and characterization of an *M. smegmatis* mutant resistant to both DCS and vancomycin though the molecular basis of the resistance mechanism remains unknown. In previous studies, we identified a spontaneous DCS-resistant *M. smegmatis* mutant with a promoter-up mutation in the alr gene, resulting in the overproduction of the Alr enzyme (Caceres et al., 1997). Alr was shown to be inhibited by DCS in a concentration-dependent manner, and DCS resistance could be conferred to pathogenic mycobacteria carrying the *M. smegmatis* alr gene in a multicopy plasmid. In addition, DCS was shown to competitively inhibit the native Ddl enzyme from *M. tuberculosis* (David et al., 1969). Belanger et al. (2000) reported the characterization of a temperature-sensitive *M. smegmatis* mutant with a single amino acid substitution in Ddl. The mutant was more susceptible to DCS, and the temperature sensitivity phenotype was due to the decreased activity of the mutated enzyme.

Recently, we observed that *M. smegmatis* alr null mutants are not dependent on D-alanine for growth, suggesting the existence of another pathway for D-alanine biosynthesis (Chacon et al., 2002). In addition, the alr null mutant is hypersusceptible to DCS, suggesting that a lethal target other than Alr is responsible for the bactericidal effect of DCS.

In order to develop novel antimicrobial agents structurally related to DCS, the lethal target(s) of DCS need to be identified and methods of screening for inhibition need to be developed.

BRIEF SUMMARY OF THE INVENTION

In this study, we investigated the roles of both Alr and Ddl in the mechanisms of action of and resistance to DCS in *M. smegmatis*. We demonstrate that Ddl activity is inhibited by DCS in a concentration-dependent manner. Overexpression of the ddl gene confers resistance to DCS but not to β-chloro-D-alanine (βCDA), an inhibitor of D-alanine racemase. Furthermore, a strain overexpressing both the alr and ddl genes displayed an increased level of resistance to DCS. Analysis of the intracellular alanine pools in wild-type and recombinant *M. smegmatis* strains demonstrated that Ddl activity is not significantly affected by DCS at concentrations inhibiting Alr.

The present invention is directed to recombinant mycobacterial strains which overproduce D-alanine ligase (Ddl), to cloned isolated genes encoding Ddl, and to the uses of the recombinant strains, and heterologous proteins.

In one aspect of the present invention, recombinant *M. smegmatis* strains expressing heterologous or overexpressing native Ddl are provided. In one embodiment of this aspect, the Ddl is the product of *M. smegmatis* ddl gene. In another embodiment, the Ddl is the product of *M. tuberculosis* ddl gene. In yet another embodiment, the Ddl is the product of both *M. smegmatis* and *M. tuberculosis* ddl genes.

In another aspect of the invention, purified recombinant Ddl is provided.

In a further aspect of the invention, cell-free methods for screening for antimicrobial agents which target the D-alanine ligase, an enzyme in the D-alanine branch of mycobacterial peptidoglycan synthesis are provided. In one embodiment of this aspect, the antimicrobial agent is structurally related to D-cycloserine. In another embodiment, the antimicrobial agent is unrelated to DCS. In a further embodiment of this aspect, the screening method employs a thin-layer chromatography assay to detect Ddl enzyme activity. In yet another embodiment, the screening method employs a phosphate release assay.

In another aspect of the invention, in vitro methods for detecting bactericidal activity of compounds against pathogenic mycobacteria are provided. The methods comprise the use of overexpressing recombinant mycobacterial strains In one embodiment of this aspect, the recombinant mycobacterial strain is GPM259. In another embodiment, the recombinant strain is GPM260. In a further embodiment, the recombinant strain is GPM265.

DETAILED DESCRIPTION OF PREFERRED EMBODIMENT

Figure 1:
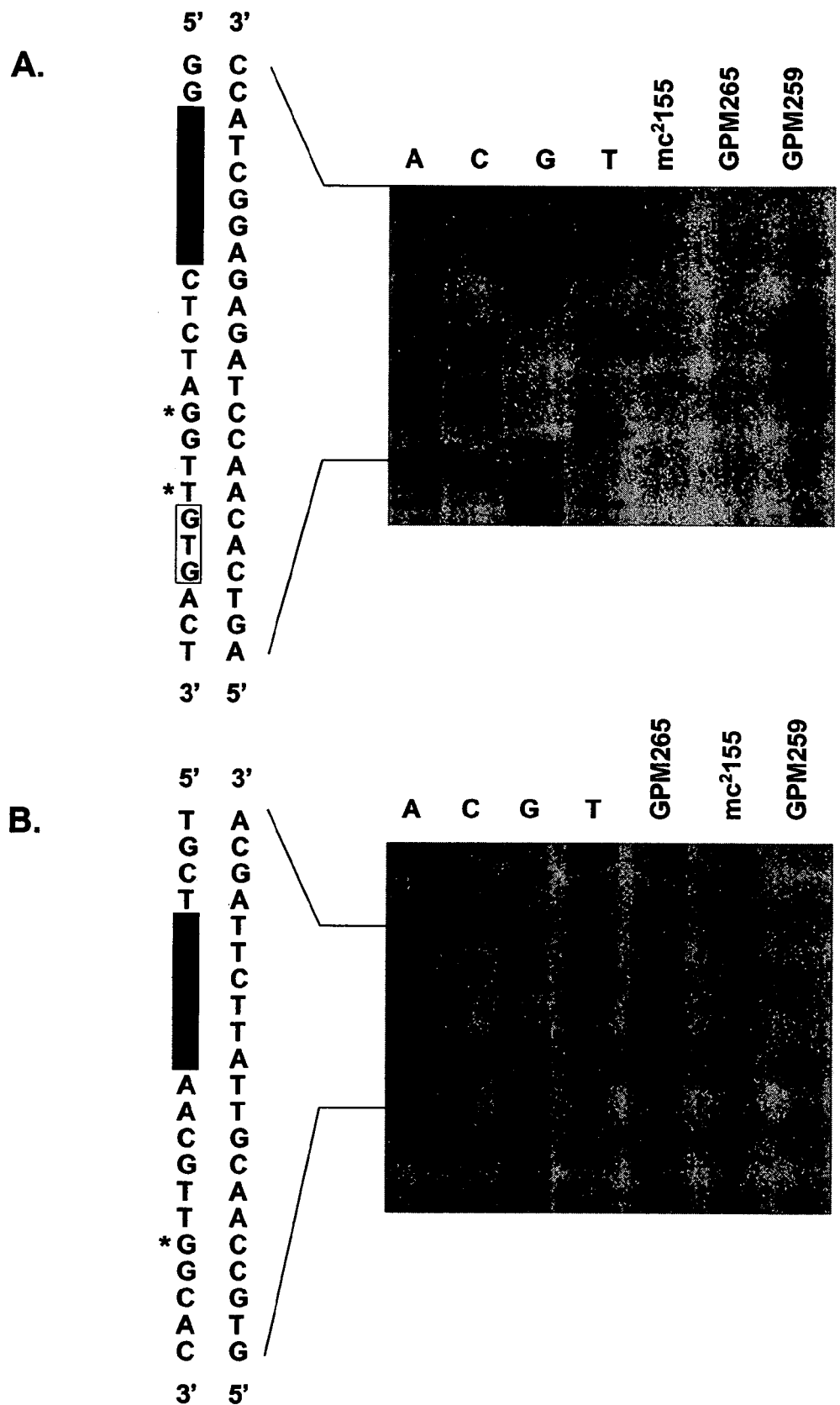
FIG. 1 shows primer extension analysis of the M. smegmatis and M. tuberculosis ddl transcripts. Total RNA (40 µg) from mc$^2$155, GPM259, and GPM265 was annealed with primer SMDDLPE (A) or TBDDLPE (B) and extended as described in Materials and Methods. Lanes A, C, G, and T display a dideoxy sequencing ladder with the corresponding primer. Asterisks, transcriptional start sites. The putative—10 boxes are highlighted. The start codon (GTG) for the M. smegmatis ddl gene is boxed.

D-Cycloserine (DCS) targets the peptidoglycan biosynthetic enzymes D-alanine racemase (Alr) and D-alanine:D-alanine ligase (Ddl). Previously, we demonstrated that the overproduction of Alr in Mycobacterium smegmatis determines a DCS resistance phenotype. As described in further detail herein, we investigated the roles of both Alr and Ddl in the mechanisms of action of and resistance to DCS in M. smegmatis. It was discovered that the overexpression of either the M. smegmatis or the Mycobacterium tuberculosis ddl gene in M. smegmatis confers resistance to DCS, but at lower levels than the overexpression of the alr gene. Furthermore, a strain overexpressing both the alr and ddl genes displayed an eightfold-higher level of resistance. The alanine pools in M. smegmatis wild-type and recombinant strains with or without DCS treatment were determined. Alr-overproducing strain GPM14 cells not exposed to DCS displayed almost equimolar amounts of L- and D-alanine in the steady state. The wild-type strain and Ddl-overproducing strains contained a twofold excess of L- over D-alanine. In all strains, DCS treatment led to a significant accumulation of L-alanine and a concomitant decease of D-alanine, with approximately a 20-fold excess of L-alanine in the Ddl-overproducing strains. These data suggest that Ddl is not significantly inhibited by DCS at concentrations that inhibit Alr. The present invention is based on the above discoveries which suggest that Ddl is the lethal target of DCS and thus allow for identification of novel drugs targeting the D-alanine branch of mycobacterial peptidoglycan biosynthesis.

The publications and other materials used herein to illuminate the background of the invention, and in particular cases, to provide additional details respecting the practice, are incorporated by reference and for convenience are referenced in the following text by author and date and are listed alphabetically by author in the appended List of References.

DEFINITIONS

The present invention employs the following definitions:

"alrA" and "alr" refer to the D-alanine racemase gene, including normal alleles of the alrA gene.

"Alr" and "Alr" refer to D-alanine racemase enzyme.

"Displays increased susceptibility to antimycobacterial agent" refers to a reduction in the minimal inhibitory concentration of the mutant strain when compared with the wild type strain.

"DCS" and "D-cycloserine" refer to 4-amino-3-isoxayolidinone.

"ddl" refers to the D-alanine ligase gene including normal alleles of the ddl gene.

"Ddl" refers to D-alanine-D-alanine synthetase, which is also referred to as D-alanine ligase.

"Isolated polypeptide" refers to a polypeptide produced as an expression product of an isolated and manipulated genetic sequence, even if expressed in a homologous cell type. Synthetically made forms or molecules expressed by heterologous cells are inherently isolated molecules.

In previous studies, a genomic library from a DCS-resistant mutant constructed in a multicopy plasmid was introduced into the wild-type M. smegmatis strain and clones resistant to 300 µg of DCS ml$^{-1}$ were selected and isolated (Caceres et al., 1997). Using this strategy, we did not identify a recombinant clone carrying the ddl gene. Since target overproduction determines a drug resistance phenotype, this outcome was unexpected. To exclude any possible bias in this library, we also screened a M. smegmatis cosmid library in a similar manner. Surprisingly, a DCS resistant clone carrying the ddl gene was still not identified. Lowering the DCS concentration resulted in a high background of DCS-sensitive colonies. These data suggest that either the overexpression of the ddl gene is toxic to the host or that the level of overexpression is not sufficient to confer a selectable resistance phenotype under the selection conditions described. To test these hypotheses, the M. smegmatis and M. tuberculosis ddl genes were amplified from genomic DNA and cloned into the E. coli-Mycobacterium shuttle vector pMV262, carrying a kanamycin resistance marker. Recombinant plasmids were introduced into M. smegmatis, and kanamycin-resistant transformants were isolated.

In this study, we demonstrated that Ddl enzyme activities in crude extracts were inhibited by DCS in a concentration-dependent manner, similar to the effect observed for the Alr enzyme (Caceres et al., 1997). Approximately 50% of Ddl enzyme activity is inhibited by DCS at a concentration of 200 µg ml, while only 10 to 15% of the Ddl activity is inhibited at 50 µg ml, near the MIC. The apparent discrepancy reflects the difference between in vivo and in vitro conditions. In live bacilli, DCS also inhibits Alr, resulting in a limited supply of D-Ala, which is the substrate for Ddl, while in the cell-free assay, D-Ala is provided in excess. These data confirmed that the mycobacterial Ddl enzyme is a target of DCS.

Overexpression of either the M. smegmatis or M. tuberculosis ddl gene, using the same expression vectors as those used to overexpress Alr (Caceres et al., 1997), confers an intermediate level of resistance to DCS. Furthermore, GPM260, a recombinant strain of M. smegmatis overproducing both Alr and Ddl, was constructed and characterized. GPM260 displayed a higher level of resistance to DCS than its parent strain, GPM14, which is consistent with the increased DCS resistance levels of S. gordonii mutants with elevated Alr and Ddl activities (Reitz et al., 1967). To test the hypothesis that inhibition of Alr by DCS decreases the intracellular pool of D-alanine, we compared the levels of D-alanine pools in wild-type and recombinant M. smegmatis strains with or without DCS treatment. The results showed that DCS treatment decreased the intracellular D-alanine pools in strains with wild-type Alr activity while the Alr-overproducing strain GPM14 maintained a relatively abundant pool of D-alanine. This observation is consistent with the intermediate level of resistance to DCS of Ddl-overproducing strains. In addition, analysis of the alanine pools in Alr-Ddl-overproducing strain GPM260 suggests that, upon exposure to DCS, Alr is readily inhibited. In contrast, overproduction of Alr and/or Ddl does not have an effect on the susceptibility to vancomycin. The increased resistance of a previously isolated M. smegmatis mutant to both DCS and vancomycin (Peteroy et al., 2000) may underscore a resistance mechanism different from overproduction of Alr and/or Ddl. Regarding resistance to DCS, there has been only one fully characterized mechanism in mycobacteria involving overexpression of the alr gene (Caceres et al., 1997). In this study, we have shown that overexpression of the ddl gene also confers DCS resistance in M. smegmatis, but at levels of resistance below those for strains overproducing Alr. Therefore, we do not expect that mutational changes, for example, ddl promoter-up mutations, would play an important role in the emergence of naturally DCS-resistant strains. The presence of a mutation(s) in the ddl structural gene leading to DCS resistance has not been demonstrated and needs further investigation.

DCS targets both Alr and Ddl enzymes, but the lethal target for its bactericidal effect has not been identified M. smegmatis alr null mutants are not dependent on D-alanine for growth, indicating that there is another pathway for D-alanine biosynthesis (Chacon et al., 2002). In addition, the M. smegmatis alr mutant is hypersusceptible to DCS, underlying the existence of another lethal target, most likely Ddl. The DCS hypersensitivity phenotype of the alr mutant is also consistent with the essentiality of the M. smegmatis ddl gene, as suggested by the temperature sensitivity phenotype of a mutant carrying a single amino acid substitution in Ddl (Belanger et al., 2000) This temperature-sensitive mutant is also more susceptible to DCS, presumably due to the low activity of the mutated Ddl. Therefore, Ddl seems to be the lethal target of DCS, while the inhibition of Alr by DCS further decreases the D-alanine pool and contributes to the inhibition of Ddl. Previously, it was suggested that DCS resistance in M. tuberculosis is primarily due to mutations in the ddl gene (David et al., 1969), and it was further speculated that inhibition of Alr plays only a minor role in the mechanism of DCS action (David, 1971) Contrary to this, our data showed that Ddl is not significantly affected by DCS at the concentration that inhibits Alr. Our observation suggests that Alr overproduction contributes to the maintenance of the internal D-alanine pool, thus antagonizing the inhibition of Ddl by DCS. For the *Streptococcus faecalis* enzymes, the DCS inhibition constants for both Alr ($K_I=0.02$ mM) and Ddl ($K_I=0.9$ mM) have been determined from the purified enzymes (Neuhaus, 1967). If the $K_I$s for the mycobacterial enzymes were to follow a similar trend, an attractive hypothesis would be that the overproduction of a high-affinity DCS-binding target (Alr) would protect a more fundamental and low-affinity target, probably Ddl, from drug inhibition. In this view, the major mechanism of resistance is the overproduction of the high-affinity but dispensable target, while the bactericidal effect is due to the inhibition of the low-affinity lethal target. Our studies do not rule out the possibility that the bactericidal action of DCS may result from the inhibition of a lethal target(s) other than Ddl. Further research is necessary to assess the lethal targets in the D-alanine branch of peptidoglycan biosynthesis in mycobacteria. This information is necessary for the development of new antimycobacterial agents targeting the D-alanine pathway.

The practice of the present invention employs, unless otherwise indicated, conventional techniques of chemistry, molecular biology, microbiology, recombinant DNA and genetics. See, e.g., Maniatis et al. (1982); Sambrook et al. (1989); Ausubel et al. (1992); Guthrie and Fink (1991); Weissbach and Weissbach (1986); Zaitlin et al. (1985) and Gelvin et al. (1990).

Method of Use: Drug Susceptibility Assays

The bactericidal activity of lead compounds are evaluated in vitro. Conventional protocols for determination of drug minimum inhibitory concentration (MIC) may be used. Example ID. employs one example of such assays. For example, the mycobacterial cells taken from glycerol stock, or preferably from a single colony, are grown in either M-ADC-TW (for faster growing strains such as *M. smegmatis*) or MO-ADC-TW (for slow growing strains such as *M. avium* or *M. bovis* BCG). Growth is continued in the absence of test compound until the optical density of 600 nm reaches approximately 0.1 to 1.0. Medium is supplemented with nutrients, if necessary.

Approximately $10^5$ CFU in 0.1 ml are inoculated in triplicate onto 96-well microplates containing either serial twofold dilutions of the test compound or without, for controls. Plates are incubated at 37° C. and checked periodically for growth. MIC is determined as the lowest concentration at which there is no visible growth of bacteria. MIC is confirmed by consistent results from at least three independent cultures.

Alternatively, the bactericidal activity of the test compound can be evaluated by measuring D-lactate dehydrogenase activity present in the supernatant. D-lactate dehydrogenase is a bacterial cytosolic enzyme, and it is only released to medium after bacterial lysis. D-lactate dehydrogenase detection kits are commercially available and can be adapted easily to microplate format.

Method of Use: Inhibition Assays

The present invention is based on the evidence, reported in further detail herein: 1) that Ddl is a binding target of DCS and is inhibited in a concentration-dependent manner; 2) that Ddl is not significantly affected by DCS at the concentration that inhibits Alr; 3) that Alr overproduction contributes to the maintenance of the internal D-alanine pool, thus antagonizing the inhibition of Ddl by DCS; and 4) that a strain overexpressing alr and ddl genes displays increased level of resistance to DCS as compared to a strain overexpressing only the alr gene. These results, in view of previously reported results, indicate that Alr is a high-affinity but dispensable target of DCS, while Ddl is the low-affinity lethal target of the bactericidal action of DCS. Thus, according to the present invention, a method is provided for screening of antimycobacterial agents against Ddl by a variety of drug screening techniques.

Preferably, purified Ddl is obtained from *M. tuberculosis* ddl gene by PCR amplification and cloning into a proper expression shuttle plasmid vector, such as an *E. coli* expression vector endowed with a mycobacterial replication origin and/or promoter, and overexpressed in *M. smegmatis*. This host strain is modified by inactivation of its endogenous ddl gene, so that it only expresses the *M. tuberculosis* counterpart. The *M. tuberculosis* Ddl enzyme is purified as a polyhistidine-tagged fusion protein through a single-step affinity chromatography in large amount and its identity is verified with biochemical methods. Ddl catalyzes the reaction 2 D-alanine+ATP→D-alanyl-D-alanine+ADP+Pi. Thus the purified protein may be used in any of a variety of in vitro cell-free screen systems as are known in the art.

The thin-layer chromatography (TLC)-based D-alanine ligase assay described in Example 1 can be used, however it is time consuming and cumbersome, and not readily adaptable to microplate format suitable for high-throughput screen. A preferred assay is the phosphate release assay (such as that used in PiPer Phosphate Assay Kit from Molecular Probes) which offers high sensitivity and extraordinary adaptability. The establishment of such an assay permits the screening of thousands of compounds, including, but not limited to, D-cycloserine and modified or derivative D-cycloserine molecules, for potential inhibitors of D-alanine ligase.

Promising candidate antimycobacterial agents are further tested in vitro using *M. smegmatis* and *M. tuberculosis* reference strains (See Methods of Use: Drug Susceptibility Assays). Preferably, the overproducing strains of the present invention are used at this step to evaluate the potential bactericidal activity of the lead compounds compared with D-cycloserine. In addition, the susceptibility of the reference strains to lead compounds indicate the specific pathway or enzyme targeted.

Method of Use: Analysis of Drug Action

According to the present invention a method is provided for analyzing the in vivo metabolic change in mycobacteria upon drug treatment. The free amino acid pool is indicative of the pathways which are either shut down or activated by the test drug. In addition, the alteration of free amino acid pool, especially the abundance of L- or D-stereotype of an individual amino acid, reflect the mode of action of the drug. This method is useful compared with cumbersome biochemical characterization of various bacterial components, such as cell wall analysis and lipid analysis. Previously, amino acid analysis has been used as a tool to determine the composition of purified protein or just simply quantify the amino acid level in biological fluids, however its use has not previously been reported for analysis of drug action.

Method of Use: Vaccine Development

The present invention is also useful for the development of a novel vaccine against pathogenic mycobacteria, such as, but not limited to, *M. tuberculosis, M. bovis, M. africanum, M. microti, M. leprae, M. avium, M. intracellular, M. paratuberculosis, M. ulcerans, M. marinum*, and subspecies and genetic variants thereof. A mycobacteria can be attenuated by selection of mutants that are better suited to growth in abnormal culture conditions and are therefore less capable of growth in the host. The attenuated *mycobacterium* may have inserted therein one or more DNA molecules for stimulation of an immune response directed against polypepticles encoded by the inserted nucleic acid molecule.

Vaccines of the present invention may be formulated with conventional carriers and/or adjuvants.

For obvious practical and moral reasons, initial work in humans to determine the efficacy o experimental compositions with regard to such afflictions is infeasible. Accordingly, in the early development of any drug or vaccine it is standard procedure to employ appropriate animal models for reasons of safety and expense. The success of implementing laboratory animal models is predicted on the understanding that immunogenic epitopes are frequently active in different host species. Thus, an immunogenic determinant in one species, for example a rodent or guinea pig, will generally be immunoreactive in a different species such as in humans. Only after the appropriate animal models are sufficiently developed will clinical trials in humans be carried out to further demonstrate the safety and efficacy of a vaccine in man.

With regard to alveolar or pulmonary infections by *M. tuberculosis*, the guinea pig model closely resembles the human pathology of the disease in many respects. Accordingly, it is well understood by those skilled in the art that it is appropriate to extrapolate the guinea pig model of this disease to humans and other mammals. As with humans, guinea pigs are susceptible to tubercular infection with low doses of the aerosolized human pathogen *M. tuberculosis*. Unlike humans where the initial infection is usually controlled, guinea pigs consistently develop disseminated disease upon exposure to the aerosolized pathogen, facilitating subsequent analysis. Further, both guinea pigs and humans display cutaneous delayed-type hypersensitivity reactions characterized by the development of a dense mononuclear cell induration or rigid area at the skin test site. Finally, the characteristic tubercular lesions of humans and guinea pigs exhibit similar morphology including the presence of Langhans giant cells. As guinea pigs are more susceptible to initial infection and progression of the disease than humans, any protection conferred in experiments using this animal model provides a strong indication that the same protective immunity may be generated in man or other less susceptible mammals. Those skilled in the art will appreciate that the present invention may be practiced with various mammalian hosts including humans and domesticated animals.

A strain of mycobacteria having a regulatable promoter to control the expression of the ddl gene, whose product is responsible for the synthesis of D-alanyl-D-alanine, will provide a attenuation of the mycobacterial strain. Use of a promoter that is active in vitro but is inactive, or minimally active, in vivo will cause lysis of the mycobacterial cells and release of immunogens which generate an immunological response. Replacement of the chromosomal wild type ddl gene with a regulatable ddl gene can be accomplished by means known in the art, including the use of a conventional integrating vector such as those described herein (See Example 1).

The mycobacterial strain used may be a wild-type mycobacterial strain or, alternatively, an alr null mutant mycobacterial may be used, such as the alr mutant described in Appl'n Ser. No. U.S. 2003/0133952.

EXAMPLE 1

The present invention is further described in the following examples, which are offered by way of illustration and are not intended to limit the invention in any manner. Standard techniques known in the art or the techniques specifically described below are utilized.

Materials and Methods

A. Bacterial Strains, Plasmids, and Culture Conditions

Bacterial strains and plasmids used in this example are listed in Table 1. *E. coli* strains were grown at 37° C. in Luria-Bertani broth or agar. *M. smegmatis* strains were grown at 37° C. with shaking (200 rpm; Innova 4300 incubator shaker; New Brunswick Scientific, Edism, N.J.) in Middlebrook 7H9 broth (BBL Microbiology Systems, Cockeysville, Md.) supplemented with albumin-dextrose complex (ADC) and 0.05% Tween 80 (M-ADC-TW broth). For analysis of the intracellular amino acid pools, *M. smegmatis* was grown in a minimal medium based on the formulation of Zygmunt (1963) and modified as previously described (Chacon et al., 2002). Tryptic soy agar base (Difco Laboratories, Detroit, Mich.) was used for growth of *M. smegmatis* on solid media. Transformations of *E. coli* and *M. smegmatis* were performed by electroporation with a Gene Pulser (Bio-Rad Laboratories, Richmond, Calif.) as described previously (Foley-Thomas et al., 1995). The following antibiotics were added to the media when necessary: kanamycin (Sigma Chemical Co., St. Louis, Mo.) at 50 μg $ml^{-1}$ or carbenicillin (Sigma) at 50 μg $ml^{-1}$ for *E. coli* strains and kanamycin at 10 μg $ml^{-1}$ for *M. smegmatis* strains.

TABLE 1

Strains and plasmids used in this study

| Strain or plasmid | Description | Reference and/or source |
|---|---|---|
| *E. coli* XL10-GOLD | $Tet^r$ Δ(mcrA)183 Δ (mcrCB-hsdSMR-mrr)173 endA1 supE44 thi-1 recA1 gyrA96 relA1 lac Hte [F' proAB $lac^qZ$ ΔM15 Tn10 ($Tet^r$) Amy $Cam^r$] | Stratagene |
| *M. smegmatis* $mc^2155$ | High-transformation *M. smegmatis* mutant derived from $mc^26$ | Snapper et al., 1990 |
| *M. smegmatis* GPM2 | $mc^2155$(pMV262) | Caceres et al., 1997 |
| *M. smegmatis* GPM14 | DCS-resistant mutant derived from $mc^2155$; overproducing Alr | 5 |
| *M. smegmatis* GPM259 | $mc^2155$(pBUN250); overproducing Ddl | This work |
| *M. smegmatis* GPM260 | GPM14(pBUN250); overproducing both Alr and Ddl | This work |
| *M. smegmatis* GPM265 | $mc^2155$(pBUN276); overproducing *M. tuberculosis* Ddl | This work |

TABLE 1-continued Strains and plasmids used in this study

| Strain or plasmid | Description | Reference and/or source |
|---|---|---|
| *M. smegmatis* GPM198A | mc²155(pBUN128A) | This work |
| pCR2.1 | TA cloning vector | Invitrogen |
| pMV262 | *E. coli*-Mycobacterium shuttle plasmid | MedImmune, Inc.; |
| pBUN128A | pMV262 with a 1.4-kb insert containing the complete *M. tuberculosis* ddl gene inserted at the EcoRI site | This work |
| pBUN172 | Recombinant plasmid isolated from an *M. smegmatis* genomic library which hybridized with an internal fragment of the ddl gene | This work |
| pBUN250 | pMV262 with a 1.4-kb insert containing the complete *M. smegmatis* ddl gene inserted at the EcoRI site | This work |
| pBUN276 | pMV262 with the *M. tuberculosis* ddl gene inserted at the BamHI/HindIII site; the *M. tuberculosis* ddl gene is fused with the DNA sequence corresponding to the first 6 codons of the *M. bovis* BCG hsp60 gene | This work |

B. Oligonucleotide primers, nucleic acid manipulations, and primer extension analysis.

All oligonucleotide primers were from Integrated DNA Technologies, Inc., Coralville, Iowa. For PCR amplification of the complete ddl gene from *M. smegmatis* were SMDDLCF (5'-CGC ATA AGG CCA GGT CAG-3'(SEQ ID NO:1) and SMDDLCR (5'-CGA AAA ACC CGT CGT GC-3'(SEQ ID NO:2). The primers for PCR amplification of the ddl gene from *M. tuberculosis* were DDLATBU (5'-GCT AAG TGC CGA TCG CAA G-3'(SEQ ID NO:3) and DDLATBD (5'-ATA ACG CTG CTG CTG GGT C-3'(SEQ ID NO:4) and TBDDLEXF (5'-CGG GAT CCG TGA GTG CTA ACG AC-3'(SEQ NO:5) and TBDDLEXR (5'-CGG AAG CTT GTG CCG ATC GCA AGC-3'(SEQ ID NO:6). The primers SMDDLPE (5'-AAA CGC TCC GGA TCG AGG TTG-3'(SEQ ID NO:7) and TBDDLPE (5'-GAG ATG GCG TGC TCG TTG-3'(SEQ ID NO:8) were used in primer extension analysis for the ddl mRNA of *M. smegmatis* and *M. tuberculosis*, respectively. PCR amplifications were performed in a Perkin-Elmer GeneAmp 9600 thermal cycler (Roche Molecular Systems, Branchburg, N.J.) by using the Expand high-fidelity PCR system (Roche Molecular Biochemicals, Indianapolis, Ind.). For restriction digestions, ligations, and agarose gel electrophoresis, standard procedures previously described (Sambrook et al., 1989) were followed. Total RNA from *M. smegmatis* strains was isolated by using RNAWIZ (Ambion, Inc., Austin, Tex.) with minor modifications (Bashyam and Tyagi, 1994). Primer extension analysis of the ddl mRNA was carried out as described previously (Davis et al., 1994). The oligonucleotide was radiolabeled with [y-$^{32}$P]ATP by using T4 polynucleotide kinase (Promega, Madison, Wis.), and the reactions were extended with Moloney murine leukemia virus reverse transcriptase (Promega). Radioactivity in primer extension products was quantified with a PhosphorImager by using ImageQuant, version 3.3 (Molecular Dynamics, Sunnyvale, Calif.).

C. *M. smegmatis* genomic library construction and cloning of the *M. smegmatis* ddl gene.

Chromosomal DNA from *M. smegmatis* mc²155 was prepared as described previously (Whipple et al., 1987). For library construction, chromosomal DNA was partially digested with Sau3AI, and fragments of 3.0 to 4.0 kb were purified from 0.8% agarose. This fraction was ligated with the *E. coli*-Mycobacterium shuttle plasmid pMV262 (Connell et al., 1993), linearized with BamHI, and dephosphorylated. The ligation mixture was transformed into *E. coli* XL10-GOLD (Stratagene, La Jolla, Calif.), and approximately 6,000 recombinants were obtained for a theoretical representation of P as >99% of the *M. smegmatis* genome.

A recombinant clone carrying the *M. smegmatis* ddl gene was identified from a genomic library by colony hybridization using a species-specific probe. An internal fragment of the *M. smegmatis* ddl gene was amplified by PCR using a pair of degenerate primers, DDLF and DDLR, based on two signature peptides of bacterial Ddl enzymes (Dutka-Malen et al., 1992). This amplified fragment was verified and radiolabeled with the Rediprime II labeling system (Amersham Pharmacia Biotech, Piscataway, N.J.). For screening the library, about 10,000 colonies from the library pool were plated, transferred to the NYTRAN nylon membrane (Midwest Scientific, Valley Park, Mo.), and screened with the labeled probe as described previously (Sambrook et al., 1989). After three rounds of screening, the recombinant plasmid pBUN172 was identified and confirmed to contain the full-length ddl gene. This sequence is identical to the sequence at GenBank with accession no. AF077728 (Belanger et al., 2000) and the sequence from the unfinished *M. smegmatis* mc²155 genome [(J. Craig Center Institute)].

D. Drug Susceptibility Assays.

MICs were determined by a microdilution method described previously (Takiff et al., 1996) with minor modifications. Briefly, *M. smegmatis* cells were grown in M-ADC-TW to mid-exponential phase (optical density at 600 nm, 0.6 to 1.0). Approximately 10$^5$ CFU in 0.1 ml were inoculated in triplicate onto 96-well microplates containing serial twofold dilutions of inhibitory compounds. Plates were incubated at 37° C. and examined daily. The MIC was defined as the minimal concentration of the drug or inhibitor that prevented visible bacterial growth after 48 h. Each MIC represents the consistent result from at least three independent cultures. Amikacin, DCS, βCDA, ethambutol, and vancomycin (all from Sigma) were prepared in sterile deionized water. Rifabutin (Amersham Pharmacia) was prepared in dimethyl sulfoxide (Fisher Scientific, St. Louis, Mo.). All further dilutions of each antibiotic were prepared in growth medium. Inhibition of colony formation by DCS was evaluated as described previously in Caceres et al., (1997), which is incorporated herein by reference. Appropriate dilutions of exponentially growing M. smegmatis cells were plated onto agar containing 0 to 1,200 μg of DCS ml$^{-1}$. Colonies were counted after 5 days of incubation at 37° C. Statistical analysis was conducted using the SAS general linear model procedure (SAS Institute, Cary, N.C.).

E. Preparation of Crude Cell Extracts from M. smegmatis Strains.

M. smegmatis cells were harvested at exponential phase and concentrated 50-fold in ice-cold 50 mM Tris-HCl (pH 8.0). Cells were disrupted with a French pressure cell (Thermo Spectronic US, Rochester, N.Y.) at 14,000 lb/in$^2$. The lysate was centrifuged at 4° C. for 30 min at 30,000×g to remove cell debris. The supernatant was subjected to ultracentrifugation at 4° C. for 4 h at 110,000×g to remove the membrane fraction. The recovered supernatant was dialyzed twice against 50 mM Tris-HCl (pH 8.0) at 4° C. and sterilized by filtration through 0.22-μm-poresize filters. The protein concentration was determined by using the DC protein assay (Bio-Rad) as recommended by the manufacturer.

F. Enzyme Assays.

The crude extract was assayed for Ddl activity by a modified thin-layer chromatography (TLC)-based method described previously (Marshall and Wright, 1998). This procedure can quantitatively determine the amount of D-alanine:D-alanine dipeptide. Briefly, crude extracts (5 to 30 μg of total protein) were incubated at 37° C. for 4 h in a 50-μl final volume containing 50 mM Tris-HCl (pH 7.8), 10 mM MgCl$_2$, 10 mM KCl, 50 mM unlabeled D-alanine, 6 mM ATP, 2.5 mM glutathione, and 5.0 μCi of [1–$^{14}$C]D-alanine (100 μCi/ml; ICN Biochemicals, Inc., Costa Mesa, Calif.). For inhibition assays, DCS was added to the final concentrations of 50, 100, 200, 400, and 800 μg ml$^{-1}$. Subsequently, 10 μl of the reaction mixture was applied to cellulose-backed TLC plates (Sigma), and ascending chromatography was developed in n-butanol-acetic acid-water (12:3:5) until the solvent reached the top of the TLC plate. The plate was dried at 100° C. for 5 min, and the radioactivity corresponding to the position of the D-alanine and D-alanine: D-alanine dipeptide was measured with a PhosphorImager. Specific activity was calculated as micromoles of D-alanine consumed per milligram per minute. The alanine racemase activity was measured in the direction of the conversion of L-alanine to D-alanine by a coupled spectrophotometric method (Wijsman, 1972) with modifications (Chacon et al., 2002). Specific activity was calculated as described previously (Caceres et al., 1997).

G. Analysis of Intracellular Pools of Amino Acids.

M. smegmatis cells were grown in minimal medium until exponential phase and split into two subcultures, and DCS was added to a final concentration of 75 μg ml$^{-1}$ to one of the subcultures. After 2 h of incubation, cells were harvested at 4° C. by centrifugation, washed twice with ice-cold double-distilled water, and concentrated 50-fold. Cells were sonicated in a salt-ice-water bath with a Vibra-Cell model VC600 sonicator (Sonic and Materials, Inc., Danbury, Conn.) for 10 min at 80% power output and 50% duty cycle. The lysate was centrifuged at 4° C. for 30 min at 30,000×g to remove bacterial debris. Protein was removed from the supernatant by serial passages through YM-10 and YM-3 Centricon concentrators (Millipore Corp., Bedford, Mass.). Determination of the abundance of individual amino acids was performed at the Amino Acid Geochronology Laboratory of Northern Arizona University (Flagstaff, Ariz.) by a reverse-phase high-performance liquid chromatography (HPLC) procedure described previously (Kaufman and Manley, 1998). This procedure is able to detect nine pairs of L- and D-amino acids in the subpicomole range. For each sample, the area of the peak representing L-glutamate constituted 50 to 60% of the total area. Thus, the abundance of each amino acid was calculated as the area under the corresponding peak and expressed relative to this pool.

H. Overproduction and Purification of M. tuberculosis Ddl Enzyme

Introduction. The development of assays to screen for and characterize novel inhibitors of the M. tuberculosis Ddl enzyme requires large amounts of purified protein. Although a preliminary biochemical characterization of inhibitors could be undertaken with crude cell extracts from M. tuberculosis, a more thorough analysis of biochemical parameters require purified products. Furthermore, large amounts of the purified protein are required for crystallographic studies. One possibility is to purify the protein directly from M. tuberculosis cell extracts. However, the purification yield is low, necessitating large cultures of a serious human pathogen. Fortunately, recombinant DNA technology provides the means to produce large amount of recombinant products using hosts such as Escherichia coli, which are safe to handle, and easy to grow and manipulate genetically. In general, the E. coli system is able to synthesize the proper mycobacterial protein; however, this is confirmed for the protein of interest. The M. tuberculosis Ddl in E. coli is designated herein as r-Ddl. The corresponding biochemical properties of the native M. tuberculosis Ddl are compared with those of r-Ddl. The purify proteins are used to determine basic biochemical parameters including the inhibitory parameters for the well-known inhibitor DCS and derivatives thereof.

Likewise, the determination of biochemical parameters are performed as a means to compare the properties of r-Ddl and the native enzyme, as well as to correlate the values obtained in our study with those previously reported in classic studies of mycobacteria (David et al., 1969) and other microbial systems.

Experimental design. The M. tuberculosis ddl gene is subcloned into an E. coli overexpression vector, so that a polyhistidine-tagged Ddl protein is synthesized by the E. coli recombinant clone. The fusion protein is purified from E. coli Ddl and other endogenous components by one-step affinity chromatography based on the properties of the histidine tag. Following removal of polyhistidine, polyclonal antibodies are raised against the r-Ddl and used to purify the native M. tuberculosis Ddl from semi-purified extracts. Using biochemical assays, the kinetic parameters of $V_{max}$, $K_m$ for D-alanine, and $K_i$ for DCS for both r-Ddl and native Ddl, are measured.

To obtain large amount of M. tuberculosis Ddl enzyme, the ddl gene is PCR amplified based on the genome sequence and cloned into an E. coli expression vector to achieve a high level of expression. Preferably, the commercially available pET system (Novagen) is used. The advantage of this system is that the inserted gene will be under the control of the strong T7 promoter, allowing large quantities of protein to be produced. In the pET system, the T7 RNA polymerase gene BL21 (DE3), and is itself under the control of the lac promoter. In the presence of the inducer IPTG, T7 RNA polymerase is expressed and will initiate transcription of the ddl gene located in the plasmid. The *M. tuberculosis* ddl gene is expressed as a fusion protein with a poly-His tag at either the N- or C-terminus, for use in purification of the resulting protein by a single-step affinity chromatography. After optimization of protein expression, a large-scale experiment is performed to obtain milligram levels of purified protein. The purity and identity of the recombinant Ddl protein is verified by two-dimensional SDS-PAGE, mass spectroscopy and N-terminal sequencing, based on the deduced protein sequence and computer-predicted characteristics, including molecular weight and isoelectric point.

Primers for the *M. tuberculosis* ddl gene are designed so that the 5' ends contain the proper restriction enzyme sites to facilitate cloning. These restriction sites will be chosen using the following criteria: the sites are not present in the ddl gene; and they will produce an in-frame fusion with the His tag in the vector after cloning. Thermostable high-fidelity DNA polymerase is used to amplify the ddl gene from *M. tuberculosis* genomic DNA. The resulting PCR produce is then digested with the appropriate restriction enzymes and cloned into pET 15b following standard cloning procedures. Restriction digestion analysis and DNA sequencing of the insertional junctions is performed to ensure the correct in-frame fusion. After verification, the plasmid is transformed into *E. coli* BL21 (DE3), which carries the T7 RNA polymerase gene under the control of the lac promoter. Protein expression is induced by adding 1 mM IPTG to cultures of recombinant *E. coli* when the OD600 is between 0.5 and 1.0. Cells are harvested at various time points after induction and whole-cell crude extracts are analyzed by SDS-PAGE to detect the expression of the Ddl protein. Optimal conditions for protein production are obtained from small-scale analysis of variations in initial culture density, inducer concentration, growth temperature, agitation speed and cell density at harvest. Optimized conditions are adopted for large-scale preparation. Cells are lysed by French Press and the resulting cell lysate passed through a Ni affinity column. Recombinant protein with the His tag bound to the column is eluted and the process repeated until the protein is purified close to homogeneity. The His tag in the recombinant protein is cleaved by thrombin prior to analysis. The purity and identity of the recombinant protein is confirmed by 2-D SDS-PAGE, mass spectrometry and N-terminal sequencing.

Purification of *M. tuberculosis* native Ddl protein. The Ddl from *E. coli* and *M. tuberculosis* is purified to determine the identity of the recombinant and native proteins. Given the cytoplasmic localization of the Ddl enzyme, we plan to prepare crude cell extracts of *M. tuberculosis* H37Rv are prepared and the cytosolic fractions are separated as described above for *M. smegmatis*. If necessary, further partial purification of this crude cell extract is performed by treating the cytosolic fraction with 0.3 mg of RNase and 0.3 mg of DNase, followed by centrifugation at 100,000×g for 2 h at 4° C. in a Beckman Ultracentrifuge by using a Ti 40 rotor. To the precooled new supernatant fraction, distilled acetone is added to precipitate the lipopolyssacharide-like components. The supernatant of the acetone precipitation is centrifuged a 100,000×g for one hour to precipitate proteins. The pellet is redissolved in buffer, and the Ddl protein is further purified by affinity chromatography using the polyclonal antibodies raised against the purified r-Ddl. Most of these steps are similar to those described in the classic studies of the *M. tuberculosis* Ddl by David et al. (1969), except for the last affinity chromatography step. Alternatively, the crude cell-free extract will be concentrated and loaded on the affinity chromatography column, without additional purification steps.

Determination of kinetic parameters. Using both the TLC and the $P_i$ release assay, the type of inhibition and the corresponding kinetic parameters are determined. The $V_{max}$, $K_m$ and $K_i$ for DCS will be evaluated by the double reciprocal plot method. Preferably, the Pi assay is used because it is readily adaptable to a high throughput screen procedure.

EXAMPLE 2

Overexpression of the *M. smegmatis* and *M. tuberculosis* ddl Genes in Recombinant *M. smegmatis.*

The *M. smegmatis* ddl gene was isolated from a genomic library as described in Example 1. The DNA fragment containing the ddl gene coding sequence, including 190 bp of the 5' flanking region and 35 bp of the 3' flanking region, was amplified by PCR and ligated into the EcoRI site of pMV262 to generate pBUN250. This plasmid was electroporated into *M. smegmatis* $mc^2155$, yielding GPM259. Since pMV262 is present in *M. smegmatis* at 5 to 10 copies (Caceres et al., 1997), the ddl gene is expected to be overexpressed in the recombinant *M. smegmatis* strain due to a gene dosage effect. This was confirmed by primer extension analysis using total RNA isolated from $mc^2155$ and GPM259. Radiometric quantitation of the primer extension bands confirmed that GPM259 overproduced the ddl transcript by 25-fold compared to $mc^2155$. In both samples, two transcriptional start sites were detected, one immediately upstream and another 3 nucleotides upstream of the start codon (GTG) (FIG. 1A). Further analysis of the sequence immediately adjacent to the start codon did not reveal any significant RNA secondary structures, excluding the possibility that the two bands detected were the result of premature extension products. It has been found for the *Mycobacterium fortuitum* blaF (Timm et al., 1994) and 11 streptomycete genes (Strohl, 1992) that transcription start sites are extremely close to the start codon. This may suggest that translation initiation in both mycobacteria and streptomycetes has less-stringent requirements for the recognition of a ribosome-binding site.

Following the same strategy, we constructed an *M. smegmatis* recombinant strain, GPM198A, carrying the plasmid pBUN128A, a pMV262-based plasmid containing the *M. tuberculosis* ddl gene coding sequence, including 140 bp of the 5' flanking region and 130 bp of the 3' flanking region. Total RNA isolated from GPM198A was subjected to primer extension analysis using oligonucleotides specific to either the *M. smegmatis* or the *M. tuberculosis* ddl gene. The results revealed that this strain overexpressed the endogenous *M. smegmatis* ddl gene rather than the plasmid-carried *M. tuberculosis* ddl gene. To circumvent this problem, a different strategy was followed. Briefly, the *M. tuberculosis* ddl gene was amplified by PCR and cloned into pMV262, yielding pBUN276. In this construct, the *M. tuberculosis* ddl gene is fused in frame with the first six codons of the *Mycobacterium bovis* BCG hsp60 gene and is under the control of its promoter. Total RNA isolated from the corresponding recombinant strain, GPM265, was subjected to primer extension analysis as described above. In this case, the chromosomally encoded ddl gene in GPM265 was expressed at a level similar to the level in wild-type $mc^2155$ (FIG. 1A), while the episomal *M. tuberculosis* ddl gene was expressed at an approximately 30-fold-higher level than the chromosomally encoded ddl gene (FIG. 1B). The transcriptional start site of the *M. tuberculosis* ddl gene located on pBUN276 was identified as the G nucleotide located 183 bp upstream of the start codon of the hsp60 gene, consistent with previous observations (Stover et al., 1991). As expected, no *M. tuberculosis* ddl transcript was detected from mc$^2$155 or GPM259 total RNA.

EXAMPLE 3

Enzymatic Characterization of *M. smegmatis* Strains

Figure 2:
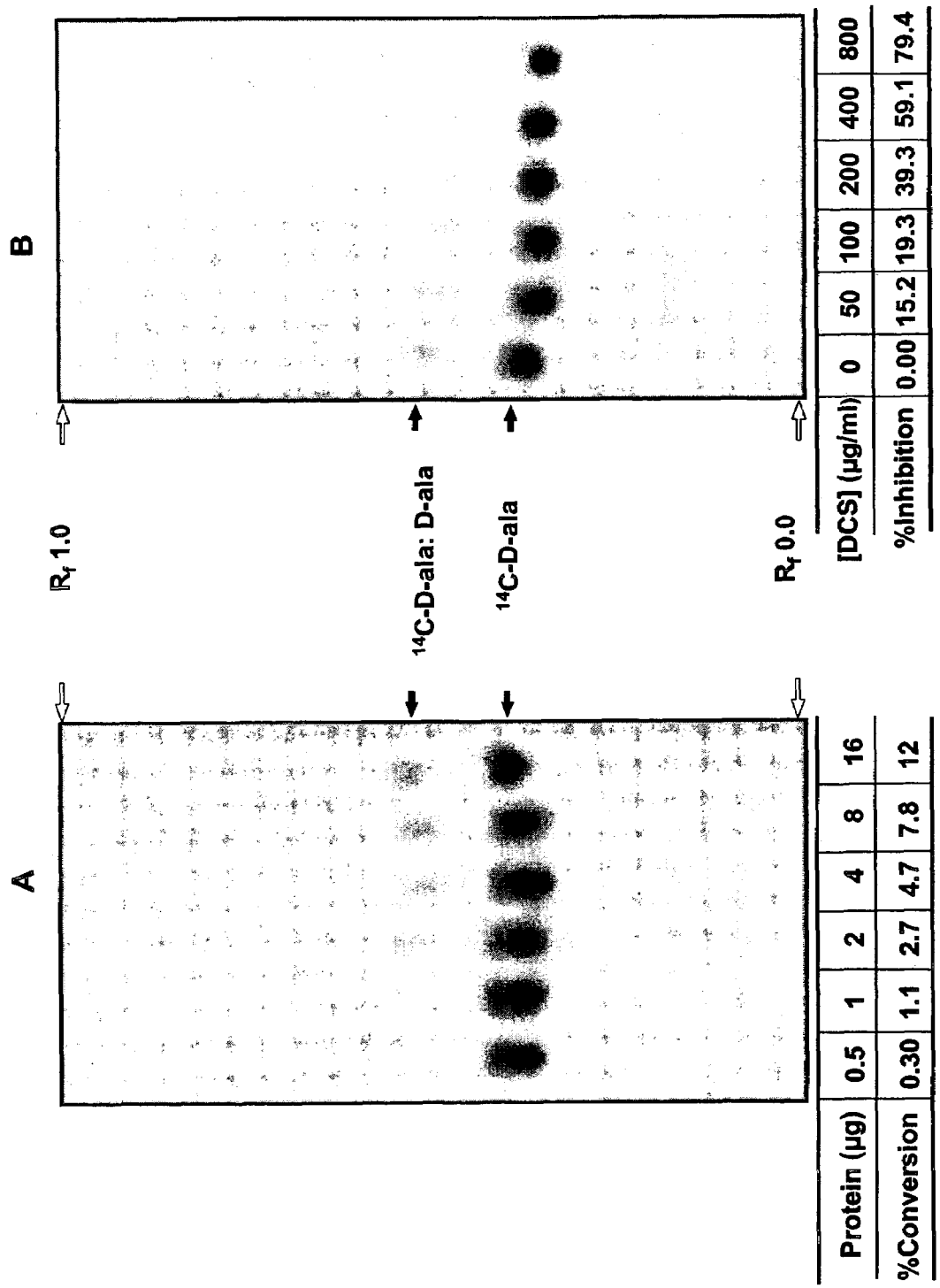
FIG. 2 shows autoradiograms of the TLC for typical Ddl assays. Ddl activities in crude extracts were determined as described in Materials and Methods. (A) Linear increase in the synthesis of the D-alanine:D-alanine dipeptide at increasing amounts of GPM259 cell extract. The percentage of conversion was defined as the percentage of the total radioactivity present in the [$^{14}$C]D-Ala: D-Ala dipeptide spot. (B) Percent inhibition of dipeptide formation (percent inhibition=100−100×[percent conversion$_{with\ DCS}$/percent conversion$_{without\ DCS}$]) in GPM259 cell extract (8 µg of total protein) at increasing concentrations of DCS.

The overexpression of the *M. smegmatis* or *M. tuberculosis* ddl gene was further confirmed by measuring Ddl enzyme activities. For this, Ddl-specific activities in cell crude extracts from mc$^2$155, GPM259, and GPM265 were determined by the TLC-based method described in Example 1. A typical autoradiogram of the TLC-based Ddl enzyme assays for strain GPM259 is shown in FIG. 2A. Ddl-specific activities in crude extracts from GPM259 and GPM265 were about 35 and 30 times greater, respectively, than that in mc$^2$155 extracts (FIG. 3A). These increases in Ddl activity were consistent with the primer extension results. As a control, Alr enzyme activities were concurrently determined by a coupled spectrophotometric method as described in Materials and Methods. As expected, cell crude extracts from mc$^2$155, GPM259, and GPM265 displayed similar Alr activities (FIG. 3B), indicating that overexpression of the ddl gene is specific and does not alter the expression of the alr gene. Furthermore, there were no observed differences between the recombinant strains overproducing Ddl and the wild-type strain regarding growth rate, growth saturation density, and colony morphology, indicating that the overexpression of the ddl gene is not toxic to the host.

Figure 4:
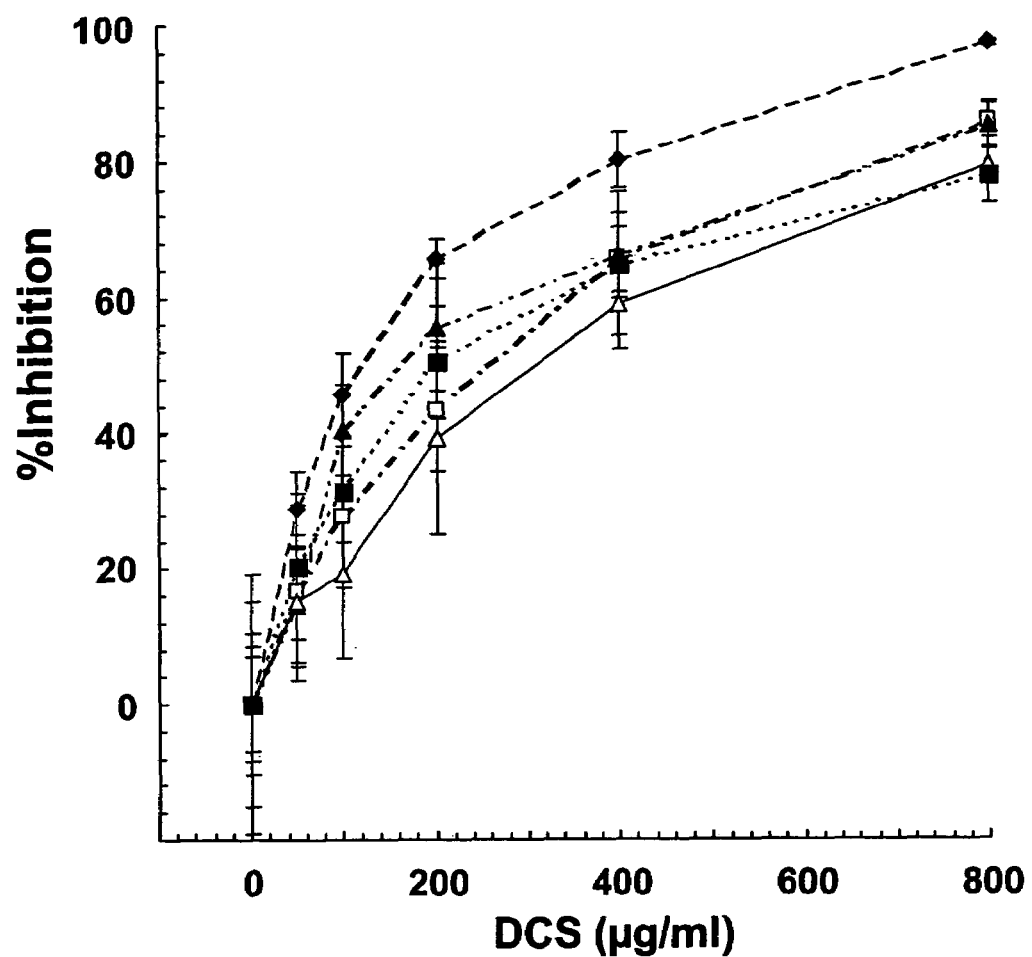
FIG. 4 shows inhibitory effect of DCS on M. smegmatis Ddl activities. Enzyme activities were determined in cell crude extracts from mc$^2$155 (solid squares), GPM14 (solid triangles), GPM259 (open triangles), GPM260 (open squares), and GPM265 (solid diamonds) in the presence of increasing concentrations of DCS. Percent inhibition was calculated (percent inhibition=100−100[SA$_{with\ DCS}$/SA$_{wthout\ DCS}$]; SA, specific activity) from three independent experiments. Statistical analysis was performed as described in Materials and Methods. The inhibition patterns can be divided into two groups (group I, mc$^2$155, GPM14, GPM259, and GPM260; group II, GPM265). A significant difference between groups was detected (P=0.02), while no significant differences within group I were detected (P=0.28).

Previously, David et al. (1969) reported that DCS competitively inhibits the *M. tuberculosis* Ddl enzyme. In this study, we performed in vitro inhibition assays to determine the Ddl-specific activities of crude extracts from mc$^2$155, GPM259, and GPM265 in the presence of increasing concentrations of DCS. A typical autoradiogram of the inhibition assay for the crude extract of GPM259 is shown in FIG. 2B. The degree of inhibition for the Ddl activities in these extracts increased proportionally to the DCS concentration (FIG. 4). No statistically significant differences between the extracts from mc$^2$155 and GPM259 were observed. However, though the inhibition of the Ddl activity in GPM265 crude extract followed a similar pattern, the percentage of inhibition was approximately 10% higher at each concentration of DCS (P<0.02). Since the primer extension analysis indicated that more than 95% of the Ddl activity present in the crude extract of GPM265 is from the expression of the *M. tuberculosis* ddl gene, this slight difference may reflect a moderately higher sensitivity of the *M. tuberculosis* Ddl enzyme to DCS inhibition. In summary, these data indicate that both *M. smegmatis* and *M. tuberculosis* Ddl enzymes are inhibited by DCS in a concentration-dependent manner and provide further evidence that Ddl is a target of this drug.

EXAMPLE 4

Drug Susceptibilities of *M. smegmatis* Strains

Figure 5:
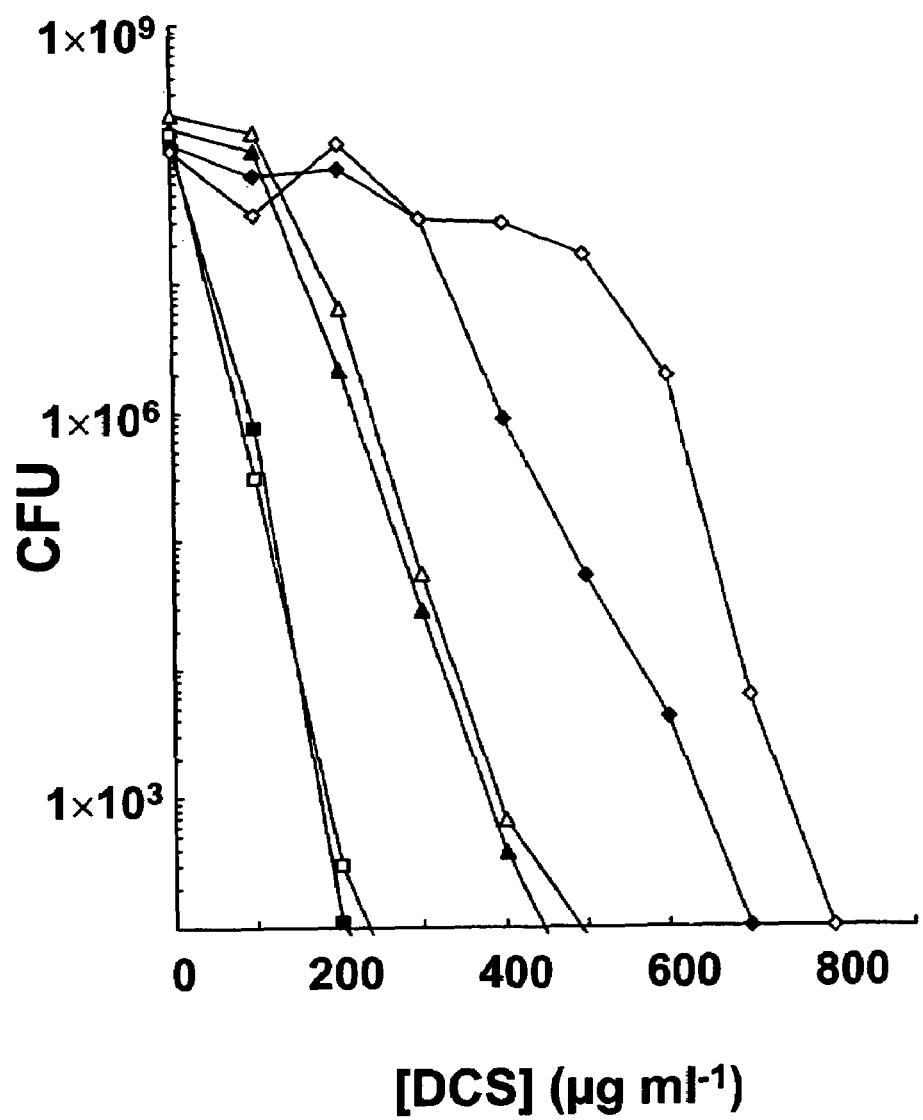
FIG. 5 shows inhibition of colony formation by DCS for various M. smegmatis strains. The curves were generated from data of a representative experiment with mc$^2$155 (solid squares), GPM2 (open squares), GPM259 (open triangles), GPM265 (solid triangles), GPM14 (solid diamonds), and GPM260 (open diamonds). Statistical analysis for three independent experiments was performed as described in Materials and Methods. Susceptibilities to DCS can be divided into four groups (group I, mc$^2$155 and GPM2; group II, GPM259 and GPM265; group III, GPM14; group IV, GPM260). Significant differences between groups were detected (group I versus group II, P<0.003; group II versus group III, P=0.025; group III versus group IV, P=0.020), while no significant differences within groups were detected (P≧0.881).

To test whether Ddl overproduction confers a DCS resistance phenotype, we evaluated the susceptibilities of *M. smegmatis* strains overproducing Ddl to DCS. The MICs of DCS for mc$^2$155, GPM259, GPM265, and GPM14 were determined (Table 2). GPM14, overproducing Alr, is a spontaneous DCS-resistant mutant derived from mc$^2$155 (Caceres et al., 1997). The MICs of DCS for strains GPM259 and GPM265 (both at 150 µg ml$^{-1}$) were twofold greater than that for mc$^2$155 (75 µg ml$^{-1}$) but were lower than that for GPM14 (300 µg ml$^{-1}$). Thus, recombinant strains overproducing Ddl showed increased levels of resistance to DCS but were not as resistant as the Alr-overproducing strain GPM14. The susceptibilities of these strains to 13CDA, which interferes with the incorporation of D-alanine into the bacterial cell wall, were also determined (Table 2). BCDA, an analog of D-alanine, was reported to target bacterial alanine racemases and transaminases (Manning et al., 1974) and showed a synergistic effect with DCS against *M. tuberculosis* (David, 2001). In this study, only the strain overproducing Alr showed increased resistance to BCDA, as the MIC for GPM14, 100 µg ml$^{-1}$, is fourfold higher than those for other strains with wild-type levels of Alr. These data are consistent with the mode of action of βCDA, which inhibits the Alr enzyme. In addition, susceptibilities to other antimicrobial agents targeting cell wall biosynthesis (ethambutol and vancomycin), RNA synthesis (rifabutin, a structural analog of rifampin with higher antimycobacterial activity), and protein synthesis (amikacin) of these *M. smegmatis* strains were identical. The DCS resistance phenotype of the Ddl-overproducing strains was further confirmed by plating bacteria on solid agar containing various concentrations of DCS. Consistent with the MIC data, GPM259 and GPM265 are more resistant to DCS than the wild-type mc$^2$155 but less resistant than the Alr-overproducing strain GPM14 (FIG. 5). Furthermore, this type of intermediate level of resistance to DCS is not related to Alr, since crude extracts from both GPM259 and GPM265 contained a wild-type level of Alr activity (FIG. 3B). Therefore, overproduction of the Ddl enzymes leads to a DCS resistance phenotype in *M. smegmatis*. However, this level of resistance may not suffice for selection of DCS-resistant clones by following the strategy described above.

EXAMPLE 5

Figure 3:
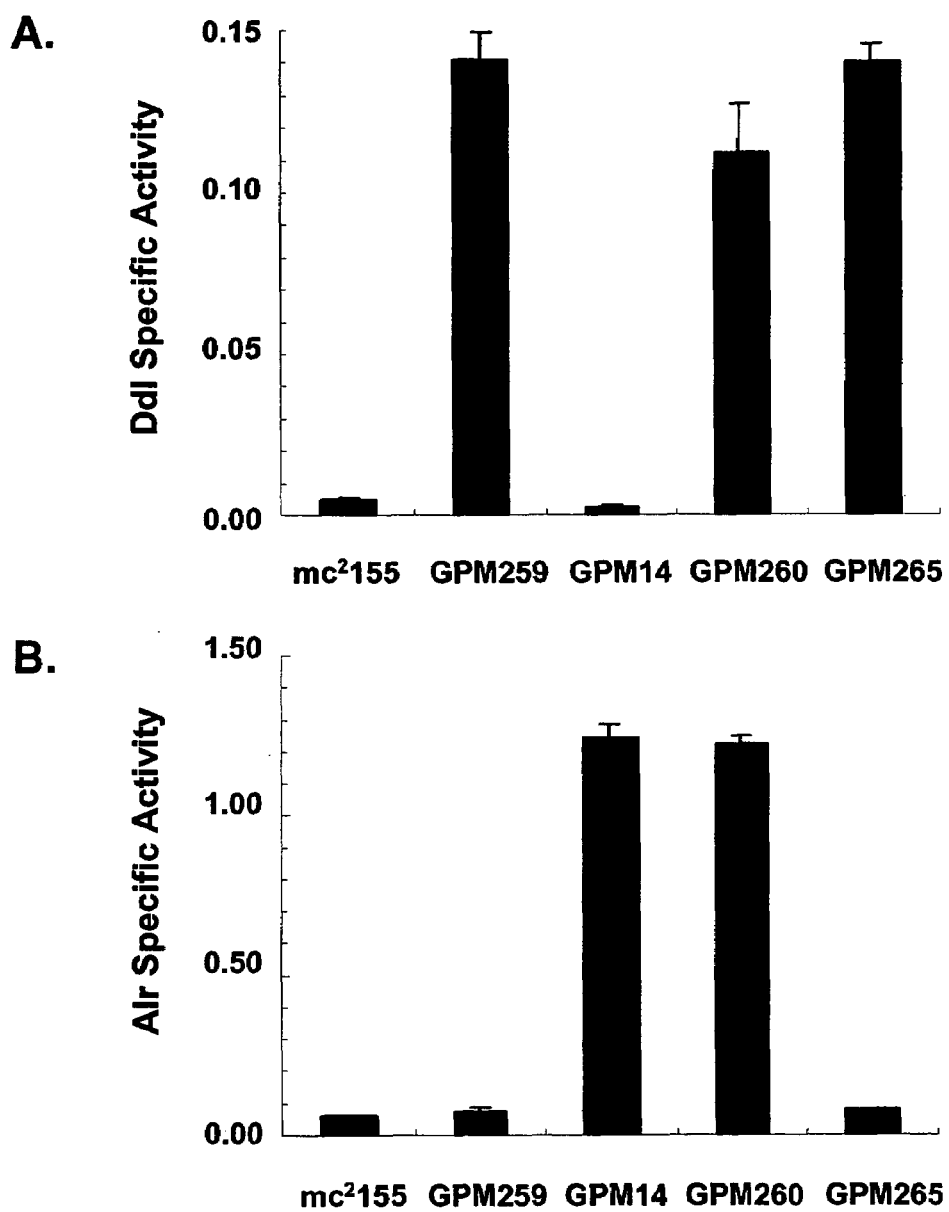
FIG. 3 shows analysis of Dir and Alr activities in M. smegmatis strains. Specific activities for Ddl (A) and Alr (B) in crude extracts were determined as described in Materials and Methods. Specific activities are expressed as micromoles of substrate (L-alanine for Alr enzyme assay and D-alanine for Ddl enzyme assay) per milligram per minute (means±standard deviations of triplicate measurements).

Construction and Characterization of an Alr-Ddl-overproducing Mycobacterial Strain It has been reported previously that a specific type of DCS-resistant *Streptococcus gordonii* mutants displayed elevated Alr and Ddl activities and that the level of resistance to DCS is higher than that for mutants with elevated Alr activity only (Reitz et al., 1967). To test the effect of the overproduction of both Alr and Ddl in *M. smegmatis* on DCS susceptibility, we introduced the multicopy plasmid pBUN250 carrying the ddl gene into the Alr-overproducing strain GPM14. As expected, the resulting strain, GPM260, overproduced both Alr and Ddl as demonstrated by enzymatic characterization (FIG. 3). In addition, the degree of inhibition of the Ddl activities in extracts from GPM260 and its parental strain, GPM14, increased proportionally to the DCS concentration (FIG. 4). No statistically significant differences between these extracts were observed (P>0.28). Note that the overproduction of Alr in GPM14 and GPM260 does not alter the degree of in vitro inhibition of the Ddl enzyme by DCS. Thus, increasing amounts of Alr protein do not seem to affect the inhibitory effect of DCS on Ddl activity. The susceptibilities of GPM260 to βCDA, ethambutol, vancomycin, rifabutin, and amikacin were identical to those of the parent strain, GPM14 (Table 2). However, GPM260, overproducing both Alr and Ddl, was significantly more resistant to DCS than the wild-type strain or strains overproducing only Alr or Ddl (Table 2 and FIG. 5).

TABLE 2

MICs of DCS M. smegmatis strains

| | Phenotype | | MIC[a] ($\mu g\ ml^{-1}$) | |
|---|---|---|---|---|
| Strain | Alr | Ddl | βCDA[b] | DCS[c] |
| mc²155 | wt[e] | wt | 25.0 | 75.0 |
| GPM2 | wt | wt | 25.0 | 75.0 |
| GPM259 | wt | Overproduced | 25.0 | 150 |
| GPM14 | Overproduced | wt | 100 | 300 |
| GPM260 | Overproduced | Overproduced | 100 | 600 |
| GPM265 | wt | Overproduced[d] | 25.0 | 150 |

[a]MICs were determined in M-ADC-TW media by a microdilution method as described in Materials and Methods.
[b]A chi-square test was performed for MICs obtained from at least four independent cultures. Susceptibilities to βCDA can be divided into two groups (group I, mc²155, GPM2, GPM259, and GPM265; group II, GPM14 and GPM260). Significant differences (P < 0.001) between these two groups were detected, while no significant differences (P ≥ 0.537) within each group were detected.
[c]A chi-square test was performed for MICs obtained from at least seven independent cultures. Susceptibilities to DCS can be divided into four groups (group I, mc²155 and GPM2; group II, GPM259 and GPM265; group III, GPM14; group IV, GPM260). Significant differences between these two groups were detected (group I versus group II, P = 0.001; group II versus group III, P P = 0.001; group IIIversus group VI, P = 0.008), while no significant differences within each group were detected (group I, P = 0.881; group II, P = 0.893).
[d]More than 95% of the Ddl activity in GPM265 is due to the expression of the episomal copy of the M. tuberculosis ddl gene (see text).
[e]wt, wild type.

EXAMPLE 6

Analysis of the Intracellular L- and D-alanine Pools

Figure 6:
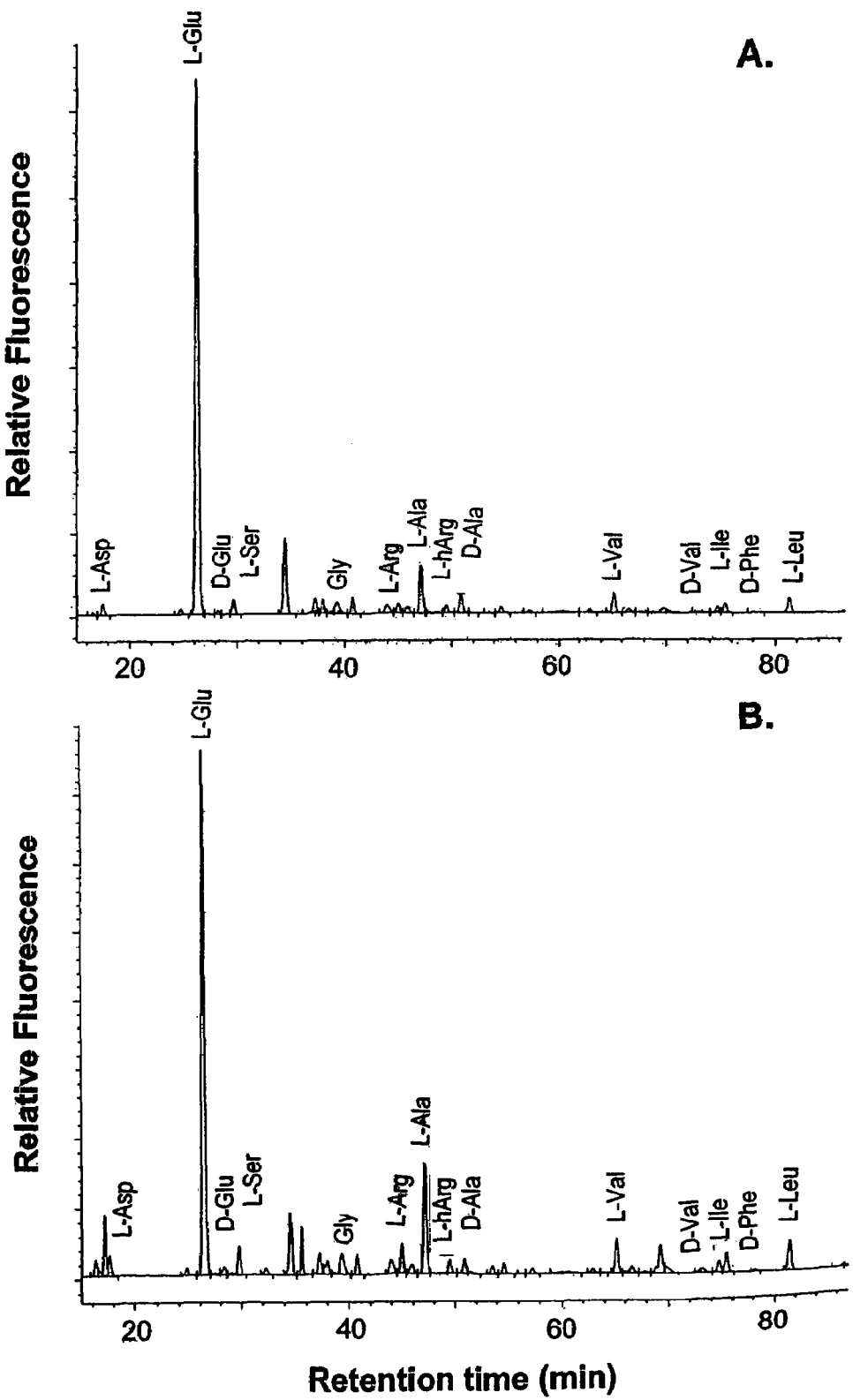
FIG. 6 shows characteristic HPLC chromatographic profiles of M. smegmatis intracellular amino acid pools. Intracellular amino acid pools of M. smegmatis mc$^2$155 untreated (A) and treated with DCS (B) were prepared and analyzed by a reverse-phase HPLC method as described in Materials and Methods. The synthetic amino acid L-homo-arginine (L-hArg) served as an internal standard for quantifying the abundance of each individual amino acid Peaks for various amino acids are indicated, with L- and D-alanine highlighted.

The incorporation of D-alanine into peptidoglycan requires the sequential interconversion of L- into D-alanine followed by the formation of the D-alanine dipeptide, reactions catalyzed by Alr and Ddl, respectively. The interplay between D-alanine biosynthesis by Alr and its consumption by Ddl contributes to the determination of the intracellular level of this amino acid. Inhibition of Alr alone would decrease the intracellular pool of D-alanine. Therefore, in live bacilli exposed to sublethal concentrations of DCS (near the MIC for the wild-type strain), if Alr is inhibited to a greater extent than Ddl, a decrease in the D-alanine pool would be expected. To test this hypothesis, we determined the intracellular alanine pools of mc²155, GPM14, GPM259, and GPM260 with and without DCS treatment by a reverse-phase HPLC. This methodology allowed detection of D- and L-alanine, L-arginine, L-asparagine/aspartate, D- and L-glutamine/glutamate (Glx), glycine, L-isoleucine, L-leucine, D-phenylalanine, L-serine, and D- and L-valine from samples prepared from cell extracts as described in Example 1 (FIG. 6). It was observed that the L-Glx pool was the most abundant, probably reflecting its crucial role in nitrogen metabolism. Moreover, this pool displayed no significant variations upon DCS treatment (P>0.63), so it was used as a standard to normalize all other intracellular pools.

Figure 7:
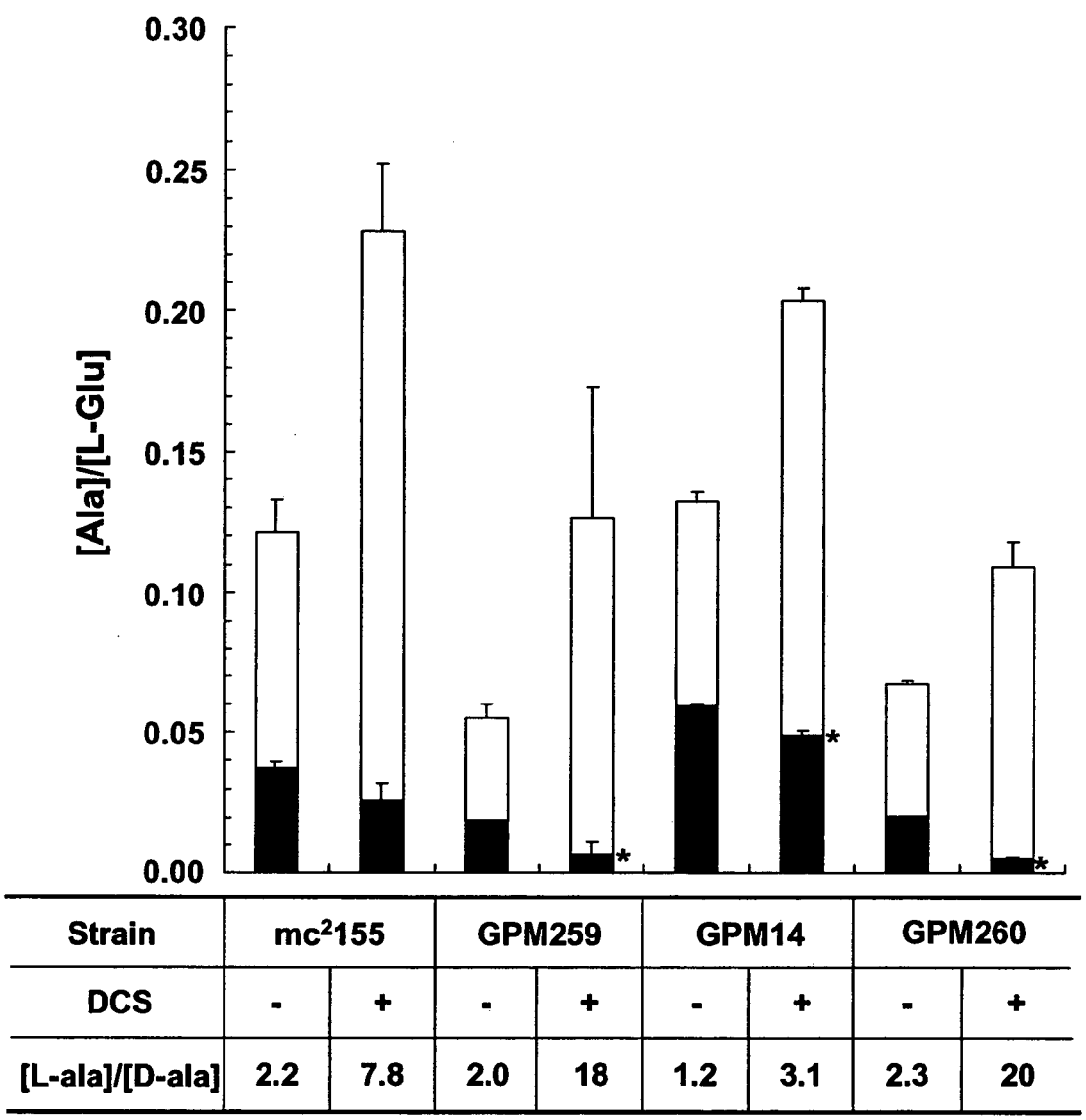
FIG. 7 shows intracellular pool of alanine in M. smegmatis strains Exponentially growing M.f smegmatis cells in minimal media were split into two subcultures, and DCS was added to a final concentration of 75 µg ml$^{-1}$ to one of the subcultures Cells were harvested after 2 h of incubation, and intracellular amino acid pools were determined as described in Materials and Methods The intracellular pool of alanine (full-length bars) is expressed relative to the L-glutamate pool ([Ala]/L-Glu]). The relative abundance of each stereoisomer in the pool is also shown by open (L-alanine) and solid (D-alanine) bars and indicated in the table at the bottom. Values shown are means±standard deviations of three independent experiments. Analysis of variance was used to compare values for total alanine, L-alanine, and D-alanine pools in each strain for both DCS-treated and untreated cells. Significant differences were observed for the L-alanine pools (P=0.03). For D-alanine pools, significant differences (asterisks) were observed only for strains GPM259 (P<0.05), GPM14 (P<0.01), and GPM260 (P<0.01).

Comparison of the amino acid pools in each strain upon DCS exposure revealed that this treatment had a specific effect on the intracellular alanine pools (FIG. 7). In all strains tested, DCS treatment led to a significant accumulation of L-alanine (P<0.03) and a concomitant decrease of D-alanine. The observed decrease of the D-alanine pool is statistically significant for strains GPM259 (P=0.05), GPM14 (P=0.01), and GPM260 (P=0.01). For strain mc²155, the decrease of the D-alanine pool fell below the statistically significant level (P>0.11). However, this strain displayed the maximum accumulation of L-alanine, and the L-alanine-to-D-alanine molar ratio increased 3.5-fold (P<0.01).

The intracellular pools of D- and L-alanine were also dependent on the steady-state production levels of Alr and Ddl enzymes. In cells not exposed to DCS, a twofold excess of the L-stereoisomer was observed for strains mc²155, GMP259, and GPM 260 (P=0.30) but strain GPM14 displayed almost equimolar amounts of both isomers, a result significantly different from those for the rest of the strains (P<0.01). These data suggest that the overproduction of Alr favors the maintenance of a relatively abundant pool of D-alanine. Treatment with DCS led to the most significant changes, as observed by comparing effects among different strains. In the wild-type strain mc²155, an eightfold excess of L- over D-alanine was observed. In the Alr-overproducing strain GPM14, only a three-fold excess was observed, representing a statistically significant difference from the wild-type strain (P<0.02). In contrast, the Ddl-overproducing strains GPM259 and GPM260 displayed an 18- to 20-fold excess of L-alanine. This result indicated that there were no significant differences between GPM259 and GPM260 (P>0.80) but that these two strains differed significantly from both the wild-type strain (P=0.04) and GPM14 (P=0.01). Furthermore, these changes are mostly determined by a significant reduction in the D-alanine pool compared to the values for the wild-type strain mc²155 (P=0.03) and GPM14 (P=0.01). These observations suggest that, in the Ddl-overproducing strains GPM259 and GPM260, Ddl is not significantly inhibited by DCS at concentrations that inhibit Alr. Moreover, the inhibition of Alr by DCS was quite effective, since the Alr-Ddl-overproducing strain GPM260 displayed values for both the D- and L-alanine pools similar to those displayed by strain GPM259, with wild-type Alr levels and overexpression of DdL.

EXAMPLE 7

High Throughput Screening of Potential Ddl Inhibitors

D-alanine ligase (Ddl) activity is determined in a cell-free phosphate release assay (Piper Phosphate Assay Kit, Molecular Probes). This assay measures the amount of inorganic phosphate generated during the production of D-alanyl-D-alanine. Purified M. tuberculosis Ddl enzyme (Example 1H.) is used in the assay to reduce background and increase sensitivity of the assay. The assay is performed according to manufacturers instructions.

Promising lead drug candidates are further tested in vitro using reference mycobacterial strains, such as M. smegmatis and M. tuberculosis Ddl overproducing strains, GPM259, GPM260, and GPM265, to evaluate the potential mycobactericidal activity of the lead compounds compared to DCS.

EXAMPLE 8

Construction of Live-attenuated Vaccine Against *Mycobacterium tuberculosis*

Vaccine development starts with virulent M. tuberculosis microorganisms from which attenuated mutants are generated. These mutants preferably carry at least two attenuating deletion mutations and no antibiotic resistant markers, so as to avoid unwanted reversions or transfers of drug-resistance. Vaccine strains may include one or more additional mutations. The vaccine strain is optionally potentiated by co-administration of cytokines or by endowing the engineered strain with the capability to produce cytokines or phagosome membrane disrupters, such as lysteriolysin. Preferably, temporal expression of these genes is regulated by promoters solely active inside phagocytic cells.

A strain of M. tuberculosis is constructed which is merodiploid, with an episomal copy of the ddl gene under the control of a promoter that is not expressed in vivo. The chromosomal copy of the native ddl gene is inactivated by means known in the art, such as point mutation or by addition, deletion, or substitution of one or more base pairs, preferably by deletion of one or more base pairs. The resulting strain is able to grow in synthetic medium but is unable to grow in vivo, because D-alanyl-D-alanine is not synthesized. As a result the cells undergo spontaneous lysis, releasing immunodominant B and T cell antigens. The strain may further include inactivation of the alr gene and/or may include genes for recombinant foreign antigens.

Such strains would be useful for the generation of attenuated live-attenuated vaccine candidates against tuberculosis and other human or animal diseases caused by mycobacteria such as leprosy, Johne's disease, and possibly Crohn's disease. Because such strains are impaired in the ability to synthesize the basic building block of cell walls, peptidoglycan, the strains undergo spontaneous lysis in vivo. Lysis provides improved antigen delivery and containment of the vaccine strain.

DEPOSIT INFORMATION

The plasmid pBUN276 has been deposited with the American Type Culture Collection (ATCC), 10801 University Boulevard, Manassas, Va. 20110-2209, USA, on Jan. 26, 2007 in accordance with the Budapest Treaty and have been accorded accession number PTA-8190.

From the foregoing it will be seen that this invention is one well adapted to attain all ends and objectives hereinabove set forth, together with the other advantages which are obvious and which are inherent to the invention.

Since many possible embodiments may be made of the invention without departing from the scope thereof, is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and sub-combinations are of utility and may be employed without reference to other features and sub-combinations. This is contemplated by and is within the scope of the claims.

REFERENCES

Ausubel et al., 1982. Current Protocols in Molecular Biology (John Wiley & Sons, New York, N.Y.)

Bashyam and Tyagi, 1994. An efficient and high-yielding method for isolation of RNA from mycobacteria. BioTechniques 17:834-836.

Belanger and Inamine, 2000. Genetics of cell wall biosynthesis, p. 191-202. In G. F. Hatfull and W. R. J. Jacobs (ed.), Molecular genetics of mycobacteria. ASM Press, Washington, D.C.

Belanger, et al., 2000. Genetic analysis of peptidoglycan biosynthesis in mycobacteria: characterization of a ddlA mutant of Mycobacterium smegmatis. J. Bacteriol. 182:6854-6856.

Brennan and Nikaido, 1995. The envelope of mycobacteria. Annu. Rev. Biochem. 64:29-63.

Caceres et al., 1997. Overexpression of the D-alanine racemase gene confers resistance to D-cycloserine in Mycobacterium smegmatis. J. Bacteriol. 179:5046-5055.

Chacon et al., 2002. Mycobacterium smegmatis D-alanine racemase mutants are not dependent on D-alanine for growth. Antimicrob. Agents Chemother. 46:47-54.

Connell et al., 1993. Effective immunization against cutaneous leishmaniasis with recombinant bacille Calmette-Guerin expressing the Leishmania surface proteinase gp63. Proc. Natl. Acad. Sci. USA90:11473-11477.

David, 1971. Resistance to D-cycloserine in the tubercle bacilli: mutation rate and transport of alanine in parental cells and drug-resistant mutants. Appl. Microbiol. 21:888-892.

David et al., 1969. Susceptibility of mycobacterial D-alanyl-D-alanine synthetase to D-cycloserine. Am. Rev. Respir. Dis. 100:579-581.

David, 2001. Synergic activity of D-cycloserine and ss-chloro-D-alanine against Mycobacterium tuberculosis. J. Antimicrob. Chemother. 47:203-206.

Davis et al., 1994. Basic methods in molecular biology, 2nd ed. Appleton & Lange, Norwalk, Conn.

Dutka-Malen et al., 1992. Sequence of the vanc gene of Enterococcus gallinarum BM4174 encoding a D-alanine:D-alanine ligase-related protein necessary for vancomycin resistance. Gene 112:53-58.

Farmer, 2001. DOTS and DOTS-plus: not the only answer. Ann. N. Y. Acad. Sci. 953:165-184.

Foley-Thomas et al., 1995. Phage infection, transfection and transformation of Mycobacterium avium complex and Mycobacterium paratuberculosis. Microbiology 141:1173-1181.

Gelvin et al. (eds) 1990. Plant Molecular Biology: Manual. Kluwer Academic Press, Dordrecht, Netherlands.

Guthrie and Fink, 1991. Guide to Yeast Genetics and Molecular Biology (Academic Press).

Kaufinan and Manley, 1998. A new procedure for determining enantiomeric (D/L) amino acid ratios in fossils using reverse phase liquid chromatography. Quat. Sci. Rev. 17:987-1000.

Lambert and Neuhaus, 1972. Mechanism of D-cycloserine action: alanine racemase from Escherichia coli W. J. Bacteriol. 110:978-987.

Maniatis et al., 1982. Molecular Cloning: A Laboratory Manual (Cold Spring Harbor Laboratory, Cold Spring Harbor, N.Y.).

Manning et al., 1974. Inhibition of bacterial growth by beta-chloro-D-alanine. Proc. Natl. Acad. Sci. USA 71:417-421.

Marshall and Wright, 1998. DdlN from vancomycin-producing Amycolatopsis orientalis C329.2 is a VanA homologue with D-alanyl-D-lactate ligase activity. J. Bacteriol. 180:5792-5795.

Neuhaus, 1967. D-cycloserine and O-carbamyl-D-serine, p. 40-83. In D. Gottlieb and P. L. Shaw (ed.), Antibiotics, mechanisms of action, vol. 1. Springer-Verlag, Heidelberg, Germany.

Peteroy et al., 2000. Characterization of a *Mycobacterium smegmatis* mutant that is simultaneously resistant to D-cycloserine and vancomycin. Antimicrob. Agents Chemother. 44:1701-1704.

Rastogi et al., 1990. Enhancement of drug susceptibility of *Mycobacterium avium* by inhibitors of cell envelope synthesis. Antimicrob Agents Chemother. 34:759-764.

Reitz et al., 1967. The biochemical mechanisms of resistance by streptococci to the antibiotics D-cycloserine and O-carbamyl-D-serine. Biochemistry 6:2561-2570.

Reyrat and Kahn, 2001. *Mycobacterium smegmatis*: an absurd model for tuberculosis? Trends Microbiol. 9:472-474.

Sambrook et al., 1989. Molecular cloning: a laboratory manual, 2nd ed. Cold Spring Harbor Laboratory Press, Cold Spring Harbor, N.Y.

Snapper et al., 1990. Isolation and characterization of efficient plasmid transformation mutants of *Mycobacterium smegmatis*. Mol. Microbiol. 4:1911-1919.

Stover et al., 1991. New use of BCG for recombinant vaccines. Nature 351:456-460.

Strohl, 1992. Compilation and analysis of DNA sequences associated with apparent streptomycete promoters. Nucleic Acids Res. 20:961-974.

Strych et al., 2001. Characterization of the alanine racemases from two *Mycobacteria*. FEMS Microbiol. Lett. 196:93-98.

Takiff et al., 1996. Efflux pump of the proton antiporter family confers low-level fluoroquinolone resistance in *Mycobacterium smegmatis*. Proc. Natl. Acad. Sci. USA 93:362-366.

Timm et al., 1994. Transcription and expression analysis, using lacZ and phoA gene fusions, of *Mycobacterium fortuitum* beta-lactamase genes cloned from a natural isolate and a high-level beta-lactamase producer. Mol. Microbiol. 12:491-504.

Tyagi and Sharma, 2002. *Mycobacterium smegmatis* and tuberculosis Trends Microbiol. 10:68-69.

Walsh, 1989. Enzymes in the D-alanine branch of bacterial cell wall peptidoglycan assembly. J. Biol. Chem. 264:2393-2396.

Weissbach and Weissbach (eds). 1986. Methods in Enzymology, Volume 118, Academic Press, Inc., Orlando, Fla.

Whipple et al., 1987. Isolation and analysis of restriction endonuclease digestive patterns of chromosomal DNA from *Mycobacterium paratuberculosis* and other *Mycobacterium species*. J. Clin. Microbiol. 25:1511-1515.

Wijsman, 1972. The characterization of an alanine racemase mutant of *Escherichia coli*. Genet. Res 20:269-277.

World Health Organization, 2000. Guidelines for establishing DOTS-Plus pilot projects for the management of multidrug-resistant tuberculosis (MDR-TB). WHO/DCS/TB/2000.279. World Health Organization, Geneva, Switzerland.

Yew et al., 1993. Adverse neurological reactions in patients with multidrug-resistant pulmonary tuberculosis after coadministration of cycloserine and ofloxacin. Clin. Infect. Dis. 17:288-289.

Zaitlin et al. (eds) 1985. Biotechnology in Plant Science, Academic Press, Inc., Orlando, Fla.

Zygmunt, 1963. Antagonism of D-cycloserine inhibition of mycobacterial growth by D-alanine. J. Bacteriol. 85:1217-1220.

What is claimed and desired to be secured by Letters Patent is as follows:

1. A recombinant plasmid pBUN276 on deposit with the American Type Culture Collection as accession number PTA-8190.

2. A transformed microorganism comprising the plasmid of claim 1.

3. The transformed microorganism of claim 2, wherein the microorganism is a naturally occurring or genetically modified *mycobacterium* strain selected from the group consisting of *M. smegmatis, M. tuberculosis, M. bovis, M. africanum, M. microti, M. leprae, M. avium, M. intracellular, M. paratuberculosis, M. ulcerans, M. marinum*, and any subspecies of said *mycobacterium* strains.

4. The transformed microorganism of claim 2, wherein the transformed microorganism is recombinant *mycobacterium* strain GPM265.

5. A recombinant plasmid, comprising at least one genomic DNA fragment encoding *M. tuberculosis* Ddl, said at least one DNA fragment fused in frame with the first six codons of *M. bovis* BCG hsp60 gene, and operably linked to the promoter of the *M. bovis* BCG hsp60 gene, wherein said at least one DNA fragment is cloned into an *E. coli-mycobacterium* shuttle vector.

6. A method for producing a recombinant microorganism comprising: transforming a *mycobacterium* with the plasmid of claim 1, and selecting, in the presence of kanamycin, the recombinant microorganism.

7. The method of claim 6, wherein the *mycobacterium* is transformed by electroporation.

8. A method of producing a microorganism with an altered level of D-alanine ligase expression relative to the corresponding non-transformed microorganism, comprising transforming the microorganism with the plasmid of claim 1.

9. A method of screening for agents which inhibit D-alanine ligase activity, comprising:

(a) exposing a culture of the recombinant *mycobacterium* strain of claim 4 to an agent to be tested to form a test culture; and (b) comparing the D-alanine ligase activity of the test culture with the D-alanine ligase activity of a control culture of the recombinant *mycobacterium* strain of claim 4 in the absence of the agent, wherein less D-alanine ligase activity in the test culture than in the control culture is indicative of inhibition of D-alanine ligase activity by the agent.

10. The method of claim 9, wherein the agent is an antimicrobial agent.

* * * * *

UNITED STATES PATENT AND TRADEMARK OFFICE
CERTIFICATE OF CORRECTION

PATENT NO. : 7,371,571 B2  Page 1 of 1
APPLICATION NO. : 10/738938
DATED : May 13, 2008
INVENTOR(S) : Raul G. Barletta et al.

It is certified that error appears in the above-identified patent and that said Letters Patent is hereby corrected as shown below:

Column 1,
Line 16, delete "USDA Cooperative State Research Service Project Grant No. NEB 14-108" and insert -- grant 98-35204-6761 -- therefor.

Column 1,
Line 18, delete "contract number" and insert -- grant -- therefor.

Column 1,
Line 19, delete "A1051176-01" and insert -- AI051176-01 -- therefor.

Signed and Sealed this

Nineteenth Day of August, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,371,571 B2 | Page 1 of 1 |
| APPLICATION NO. | : 10/738938 | |
| DATED | : May 13, 2008 | |
| INVENTOR(S) | : Raul G. Barletta et al. | |

It is certified that error appears in the above-identified patent and that said Letters Patent is hereby corrected as shown below:

Column 11,
Line 11, after "Inc;" insert --Connell et al., 1993--

Signed and Sealed this

Third Day of February, 2009

JOHN DOLL
*Acting Director of the United States Patent and Trademark Office*